US006956049B1

(12) United States Patent
Cosford et al.

(10) Patent No.: US 6,956,049 B1
(45) Date of Patent: Oct. 18, 2005

(54) METHODS OF MODULATING PROCESSES MEDIATED BY EXCITATORY AMINO ACID RECEPTORS

(75) Inventors: Nicholas D. P. Cosford, San Diego, CA (US); Ian A. McDonald, San Diego, CA (US); Stephen D. Hess, San Diego, CA (US); Mark A. Varney, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/387,135

(22) Filed: Aug. 31, 1999

(51) Int. Cl.[7] .................. A61K 31/425; A51K 31/425; C07D 277/00

(52) U.S. Cl. ...................... 514/365; 514/369; 514/370; 514/371; 514/372; 548/146

(58) Field of Search ............................... 514/362, 363, 514/365, 366, 372, 373, 430, 438, 439, 443, 514/444, 445, 447, 448, 369, 370, 371; 548/146

(56) References Cited

U.S. PATENT DOCUMENTS 5,574,036 A * 11/1996 Bernardon et al. ...... 514/239.2
6,150,413 A * 11/2000 Bernardon et al. ......... 514/568

FOREIGN PATENT DOCUMENTS

JP        56123903 A * 9/1981 .......... A01N 27/00
WO    WO-96/33181 A1 * 10/1996

OTHER PUBLICATIONS

STN/CAS online, file'HCAPLUS, Acc. No. 1987:636598, (Sakamoto et al., Chemical & Pharmaceutical Bulletin (1987), vol. 35, No. 2, pp. 823-828), Abstract.*

* cited by examiner

Primary Examiner—S. Mark Clardy
Assistant Examiner—Frank Choi
(74) Attorney, Agent, or Firm—David Rubin; David Rose

(57) ABSTRACT

In accordance with the present invention, there are provided methods of modulating the activity of excitatory amino acid receptors using a specifically defined class of heterocyclic compounds. In one embodiment, there are provided methods of modulating metabotropic glutamate receptors. The present invention also discloses methods of treating disease using heterocyclic compounds. Diseases contemplated include cerebral ischemia, chronic neurodegeneration, psychiatric disorders, schizophrenia, mood disorders, emotion disorders, disorders of extrapyramidal motor function, obesity, disorders of respiration, motor control and function, attention deficit disorders, concentration disorders, pain disorders, neurodegenerative disorders, epilepsy, convulsive disorders, eating disorders, sleep disorders, sexual disorders, circadian disorders, drug withdrawal, drug addiction, compulsive disorders, anxiety, panic disorders, depressive disorders, skin disorders, retinal ischemia, retinal degeneration, glaucoma, disorders associated with organ transplantation, asthma, ischemia and astrocytomas. The invention further discloses methods of preventing disease conditions related to diseases of the pulmonary system, diseases of the nervous system, diseases of the cardiovascular system, diseases of the gastrointestinal system, diseases of the endocrine system, diseases of the exocrine system, diseases of the skin, cancer and diseases of the ophthalmic system. The invention also discloses pharmaceutically acceptable salt forms of heterocyclic compounds.

7 Claims, No Drawings

METHODS OF MODULATING PROCESSES MEDIATED BY EXCITATORY AMINO ACID RECEPTORS

FIELD OF THE INVENTION

The present invention relates to therapeutic methods for the treatment and prevention of various disease conditions using heterocyclic compounds. In addition, the invention relates to methods of modulating processes mediated by excitatory amino acid receptors. The invention also relates to pharmaceutically acceptable salt forms of heterocyclic compounds.

BACKGROUND OF THE INVENTION

Excitatory amino acids, such as the amino acid L-glutamic acid (glutamate), are major excitatory neurotransmitters in the mammalian central nervous system. Anatomical, biochemical and electrophysiological analyses suggest that glutamatergic systems are involved in a broad array of neuronal processes, including fast excitatory synaptic transmission, regulation of neurotransmitter release, long-term potentiation, long-term depression, learning and memory, developmental synaptic plasticity, hypoxic-ischemic damage and neuronal cell death, epileptiform seizures, visual processing, as well as the pathogenesis of several neurodegenerative disorders. See generally, Nakanishi et al., *Brain Research Reviews* 26:230–235 (1998); Monaghan et al., *Ann. Rev. Pharmacol. Toxicol.* 29:365–402 (1980). This extensive repertoire of functions, especially those related to learning, neurotoxicity, and neuropathology, has stimulated recent attempts to describe and define the mechanisms through which glutamate exerts its effects.

Glutamate has been observed to mediate its effects through receptors that have been categorized into two main groups: ionotropic and metabotropic. Metabotropic glutamate receptors are divided into three groups based on amino acid sequence homology, transduction mechanism and pharmacological properties, namely Group I, Group II and Group III. Each Group of receptors contains one or more types of receptors. For example, Group I includes metabotropic glutamate receptors 1 and 5 (mGluR1 and mGluR5), Group II includes metabotropic glutamate receptors 2 and 3 (mGluR2 and mGluR3) and Group III includes metabotropic glutamate receptors 4, 6, 7 and 8 (mGluR4, mGluR6, mGluR7 and mGluR8). Several subtypes of a mGluR type may exist. For example, subtypes of mGluR1 include mGluR1$a$, mGluR1$b$, mGluR1$c$ and mGluR1$d$.

Anatomical studies demonstrate a broad and selective distribution of metabotropic glutamate receptors in the mammalian nervous system. For example, mGluR1 is expressed in the cerebellum, olfactory bulb, hippocampus, lateral septum, thalamus, globus pallidus, entopeduncular nucleus, ventral pallidum and substantia nigra (Petralia et al., (1997) *J Chem Neuroanat*, 13:77–93; Shigemoto et al., (1992) *J Comp Neurol*, 322:121–135). In contrast, mGluR5 is weakly expressed in the cerebellum, while higher levels of expression are found in the striatum and cortex (Romano et al., (1995) *J Comp Neurol*, 355:455–469). In the hippocampus, mGluR5 appears widely distributed and is diffusely expressed.

Metabotropic glutamate receptors are typically characterized by seven putative transmembrane domains, preceded by a large putative extracellular amino-terminal domain and followed by a large putative intracelluar carboxy-terminal domain. The receptors couple to G-proteins and activate certain second messengers depending on the receptor group. Thus, for example, Group 1 mGluRs activate phospholipase C. Activation of the receptors results in the hydrolysis of membrane phosphatidylinositol (4,5)-bisphosphate to diacylglycerol, which activates protein kinase C, and inositol trisphosphate, which in turn activates the inositol trisphosphate receptor to promote the release of intracellular calcium.

Ionotropic glutamate receptors are generally divided into two classes: the NMDA and non-NMDA receptors. Both classes of receptors are linked to integral cation channels and share some amino acid sequence homology. GluR1–4 are termed AMPA ($\alpha$-amino-3-hydroxy-5-methylisoxazole-4-propionic acid) receptors because AMPA preferentially activates receptors composed of these subunits, while GluR5–7 and KA1–2 are termed kainate receptors as these are preferentially sensitive to kainic acid. Thus, an "AMPA receptor" is a non-NMDA receptor that can be activated by AMPA. AMPA receptors include the GluR1–4 family, which form homo-oligomeric and hetero-oligomeric complexes which display different current-voltage relations and calcium permeability. Polypeptides encoded by GluR1–4 nucleic acid sequences can form functional ligand-gated ion channels. An AMPA receptor includes a receptor having a GluR1, GluR2, GluR3 and/or GluR4 subunit. A NMDA receptor includes a receptor having NR1, NR2$a$, NR2$b$, NR2$c$, NR2$d$ and/or NR3.

Because of the physiological and pathological significance of excitatory amino acid receptors generally and metabotropic glutamate receptors, in particular, there is a need to identify methods of modulating excitatory amino acid receptor-mediated processes, as well as therapeutic methods of treatment and methods for prevention of diseases.

BRIEF DESCRIPTION OF THE INVENTION

In accordance with the present invention, there are provided methods of modulating the activity of excitatory amino acid receptors using a specifically defined class of heterocyclic compounds. In one embodiment, there are provided methods of modulating metabotropic glutamate receptors. The present invention also discloses methods of treating disease using heterocyclic compounds. Diseases contemplated include cerebral ischemia, chronic neurodegeneration, psychiatric disorders, schizophrenia, mood disorders, emotion disorders, disorders of extrapyramidal motor function, obesity, disorders of respiration, motor control and function, attention deficit disorders, concentration disorders, pain disorders, neurodegenerative disorders, epilepsy, convulsive disorders, eating disorders, sleep disorders, sexual disorders, circadian disorders, drug withdrawal, drug addiction, compulsive disorders, anxiety, panic disorders, depressive disorders, skin disorders, retinal ischemia, retinal degeneration, glaucoma, disorders associated with organ transplantation, asthma, ischemia and astrocytomas. The invention further discloses methods of preventing disease conditions related to diseases of the pulmonary system, diseases of the nervous system, diseases of the cardiovascular system, diseases of the gastrointestinal system, diseases of the endocrine system, diseases of the exocrine system, diseases of the skin, cancer and diseases of the ophthalmic system. The invention also discloses pharmaceutically acceptable salt forms of heterocyclic compounds.

DETAILED DESCRIPTION OF THE INVENTION

In accordance with the present invention, there are provided methods of modulating the activity of excitatory amino acid receptors, said method comprising contacting said receptors with at least one compound having the structure A-L-B or enantiomers, diastereomeric isomers or mixtures of any two or more thereof, or pharmaceutically acceptable salts thereof, in an amount sufficient to modulate the activity of said excitatory amino acid receptor, wherein:

A is a 5-, 6- or 7-membered ring having the structure:

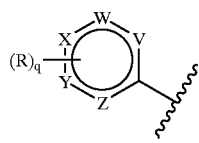

wherein at least one of V, W, X, Y and Z is $(CR)_p$, wherein p is 0, 1 or 2;
at least one of V, W, X, Y and Z is O, N or S;
the remainder of V, W, X, Y and Z are each independently O, N or S; and
each R is independently halogen, substituted or unsubstituted hydrocarbyl, substituted or unsubstituted aryl, heterocycle, mercapto, nitro, carboxyl, carbamate, carboxamide, hydroxy, ester, cyano, amide, amide, amidine, amido, sulfonyl or sulfonamide, wherein q is 0, 1, 2 or 3;
L is substituted or unsubstituted alkenylene, alkynylene, or azo; and
B is substituted or unsubstituted hydrocarbyl, substituted or unsubstituted cyclohydrocarbyl, substituted or unsubstituted heterocycle, optionally containing one or more double bonds, or substituted or unsubstituted aryl;
provided, that the following compounds are excluded: the compounds wherein A is a 6-membered ring wherein: V, W, X and Y are $(CR)_p$, wherein p is 1, Z is N;
  R at the V position is hydrogen, lower alkyl, hydroxy, hydroxy-lower alkyl, amino-lower alkyl, lower alkylamino-lower alkyl, di-lower alkylamino-lower alkyl, unsubstituted or hydroxy-substituted lower alkyleneamino-lower alkyl, lower alkoxy, lower alkanoyloxy, amino-lower alkoxy, lower alkylamino-lower alkoxy, di-lower alkylamino-lower alkoxy, phthalimido-lower alkoxy, unsubstituted or hydroxy- or 2-oxo-imidazolidin-1-yl-substitued lower alkyleneamino-lower alkoxy, carboxy, esterified or amidated carboxy, carboxy-lower alkoxy or esterified carboxy-loweralkoxy; R at the W position is hydrogen; R at the X position is hydrogen, lower alkyl, carboxy, esterified carboxy, amidated carboxy, hydroxy-lower alkyl, hydroxy, lower alkoxy or lower alkanoyloxy; and R at the Y position is hydrogen, lower alkyl, hydroxy-lower alkyl, carboxy, esterified carboxy, amidated carboxy, unsubstituted or lower alkyl-, lower alkoxy-, halo- and/or trifluoromethyl-substituted N-lower alkyl-N-phenylcarbamoyl, lower alkoxy, halo-lower alkyl or halo-lower alkoxy;
L is substituted or unsubstituted alkenylene, alkynylene or azo, and
B is substituted or unsubstituted aryl or heterocycle having two or more double bonds, wherein substituents are independently lower alkyl, lower alkenyl, lower alkynyl, phenyl, phenyl-lower alkynyl, hydroxy, hydroxy-lower alkyl, lower alkoxy, lower alkenyloxy, lower alkylenedioxy, lower alkanoyloxy, phenoxy, phenyl-lower alkoxy, acyl, carboxy, esterified carboxy, amidated carboxy, cyano, nitro, amino, acylamino, N-acyl-N-lower alkylamino, halo and halo-lower alkyl, wherein phenyl, phenyl-lower alkynyl, phenoxy, and phenyl-lower alkoxy may bear further substituents.

As employed herein, "excitatory amino acid receptors" refers to a class of cell-surface receptors which are the major class of excitatory neurotransmitter receptors in the central nervous system. In addition, receptors of this class also mediate inhibitory responses. Excitatory amino acid receptors are membrane spanning proteins that mediate the stimulatory actions of the amino acid glutamate and possibly other endogenous acidic amino acids. Excitatory amino acids are crucial for fast and slow neurotransmission and they have been implicated in a variety of diseases including Alzheimer's disease, stroke, schizophrenia, head trauma, epilepsy, and the like. In addition, excitatory amino acids are integral to the processes of long-term potentiation and depression which are synaptic mechanisms underlying learning and memory. There are three main subtypes of excitatory amino acid receptors: (1) the metabotropic receptors; (2) the ionotropic NMDA receptors; and (3) the non-NMDA receptors, which include the AMPA receptors and kainate receptors.

As employed herein, the phrase "modulating the activity of" refers to altered levels of activity so that the activity is different with the use of the invention method when compared to the activity without the use of the invention method. Modulating the activity of excitatory amino acid receptors includes the suppression or augmentation of the activity of receptors. Suppression of receptor activity may be accomplished by a variety of means, including blocking of a ligand binding site, biochemical and/or physico-chemical modification of a ligand binding site, binding of agonist recognition domains, preventing ligand-activated conformational changes in the receptor, preventing the activated receptor from stimulating second messengers such as G-proteins, and the like. Augmentation of receptor activity may be accomplished by a variety of means including, stabilization of a ligand binding site, biochemical and/or physico-chemical modification of a ligand binding site, binding of agonist recognition domains, promoting ligand-activated conformational changes in the receptor, and the like.

Excitatory amino acid receptor activity can be involved in numerous disease states. Therefore modulating the activity of receptors also refers to a variety of therapeutic applications, such as the treatment of cerebral ischemia, chronic neurodegeneration, psychiatric disorders, schizophrenia, mood disorders, emotion disorders, disorders of extrapyramidal motor function, obesity, disorders of respiration, motor control and function, attention deficit disorders, concentration disorders, pain disorders, neurodegenerative disorders, epilepsy, convulsive disorders, eating disorders, sleep disorders, sexual disorders, circadian disorders, drug withdrawal, drug addiction, compulsive disorders, anxiety, panic disorders, depressive disorders, skin disorders, retinal ischemia, retinal degeneration, glaucoma, disorders associated with organ transplantation, asthma, ischemia or astroytomas, and the like.

The compounds contemplated for use in the practice of the invention are especially useful for the treatment of mood disorders such as anxiety, depression, psychosis, drug withdrawal, tobacco withdrawal, memory loss, cognitive impairment, dementia, Alzheimer's disease, and the like; disorders of extrapyramidal motor function such as Parkinson's disease, progressive supramuscular palsy, Huntington's disease, Gilles de la Tourette syndrome, tardive dyskinesia, and the like.

Compounds contemplated for use in the practice of the invention are also especially useful for the treatment of pain disorders such as neuropathic pain, chronic pain, acute pain, painful diabetic neuropathy, post-herpetic neuralgia, cancer-associated pain, pain associated with chemotherapy, pain associated with spinal cord injury, pain associated with multiple sclerosis, causalgia and reflex sympathetic dystrophy, phantom pain, post-stroke (central) pain, pain associated with HIV or AIDS, trigeminal neuralgia, lower back pain, myofacial disorders, migraine, osteoarthritic pain, postoperative pain, dental pain, post-burn pain, pain associated with systemic lupus, entrapment neuropathies, painful polyneuropathies, ocular pain, pain associated with inflammation, pain due to tissue injury, and the like.

"Contacting" may include contacting in solution or in solid phase.

"Pharmaceutically acceptable salt" refers to a salt of the compound used for treatment which possesses the desired pharmacological activity and which is physiologically suitable. The salt can be formed with organic acids such as acetate, adipate, alginate, aspartate, benzoate, benzenesulfonate, butyrate, citrate, camphorate, camphorsulfonate, cyclopentanepropionate, digluconate, dodecylsulfate, ethanesulfonate, fumarate, glucoheptanoate, glycerophosphate, heptanoate, hexanoate, 2-hydroxyethanesulfonate, lactate, malate, maleate, methanesulfonate, 2-naphthalenesulfonate, nicotinate, oxalate, tartrate, toluenesulfonate, undecanoate, and the like. The salt can also be formed with inorganic acids such as sulfate, bisulfate, chlorate, perchlorate, hemisulfate, hydrochloride, hydrobromide, hydroiodide, and the like. In addition, the salt can be formed with a base salt, including ammonium salts, alkali metal salts such as sodium salts, potassium salts, and the like; alkaline earth metal salts such as calcium salts, magnesium salts, and the like; salts with organic bases such as dicyclohexylamine salts, N-methyl-D-glucamine, phenylethylamine, and the like; and salts with amino acids such as arginine, lysine, and the like.

Salt forms of compounds herein find several advantages. Certain pharmaceutically acceptable salt forms of heterocyclic compounds described herein, achieve higher solubility as compared with non-salt forms. In addition, certain salt forms are more compatible with pharmaceutical uses. For example, the hydrochloric acid salt of 2-(phenylethynl)-1,3-thiazole is an oil while the toluene sulfonic acid salt form of 2-(phenylethynl)-1,3-thiazole is a solid that is soluble in aqueous medium. (See Example 25.) Characteristics of salt forms of compounds depend on the characteristics of the compound so treated, and on the particular salt employed.

As employed herein, "hydrocarbyl" refers to straight or branched chain univalent and bivalent radicals derived from saturated or unsaturated moieties containing only carbon and hydrogen atoms, and having in the range of about 1 up to 12 carbon atoms. Exemplary hydrocarbyl moieties include alkyl moieties, alkenyl moieties, dialkenyl moieties, trialkenyl moieties, alkynyl moieties, alkadiynal moieties, alkatriynal moieties, alkenyne moieties, alkadienyne moieties, alkenediyne moieties, and the like. The term "substituted hydrocarbyl" refers to hydrocarbyl moieties further bearing substituents as set forth below;

"alkyl" refers to straight or branched chain alkyl radicals having in the range of about 1 up to 12 carbon atoms; "substituted alkyl" refers to alkyl radicals further bearing one or more substituents such as hydroxy, alkoxy, mercapto, aryl, heterocyclic, halogen, trifluoromethyl, pentafluoroethyl, cyano, cyanomethyl, nitro, amino, carboxyl, carbamate, sulfonyl, sulfonamide, and the like;

"alkenyl" refers to straight or branched chain hydrocarbyl radicals having at least one carbon-carbon double bond, and having in the range of about 2 up to 12 carbon atoms (with radicals having in the range of about 2 to 6 carbon atoms presently preferred), and "substituted alkenyl" refers to alkenyl radicals further bearing one or more substituents as set forth above;

"alkenylene" refers to straight or branched chain divalent alkenyl moieties having at least one carbon-carbon double bond, and having in the range of about 2 up to 12 carbon atoms, and "substituted lower alkenylene" refers to divalent alkenyl radicals further bearing one or more substituents as set forth above;

"alkynyl" refers to straight or branched chain hydrocarbyl radicals having at least one carbon-carbon triple bond, and having in the range of about 2 up to 12 carbon atoms, and "substituted alkynyl" refers to alkynyl radicals further bearing one or more substituents as set forth above;

"alkynylene" refers to straight or branched chain divalent alkynyl moieties having at least one carbon-carbon triple bond, and having in the range of about 2 up to 12 carbon atoms, and "substituted alkynylene" refers to divalent alkynyl radicals further bearing one or more substituents as set forth above;

"cyclohydrocarbyl" refers to ring-containing univalent radicals derived from saturated or unsaturated moieties containing only carbon and hydrogen atoms, and having in the range of about 3 up to 20 carbon atoms. Exemplary cyclohydrocarbyl moieties include cycloalkyl moieties, cycloalkenyl moieties, cycloalkadienyl moieties, cycloalkatrienyl moieties, cycloalkynyl moieties, cycloalkadiynyl moieties, spiro hydrocarbon moieties wherein two rings are joined by a single atom which is the only common member of the two rings, bicyclic hydrocarbon moieties wherein two rings are joined and have two atoms in common, and the like. The term "substituted cyclohydrocarbyl" refers to cyclohydrocarbyl moieties further bearing one or more substituents as set forth above;

"cycloalkyl" refers to ring-containing radicals containing in the range of about 3 up to 20 carbon atoms, and "substituted cycloalkyl" refers to cycloalkyl radicals further bearing one or more substituents as set forth above;

"cycloalkenyl" refers to ring-containing alkenyl radicals having at least one carbon-carbon double bond, and having in the range of about 3 up to 20 carbon atoms, and "substituted cycloalkenyl" refers to cyclic alkenyl radicals further bearing one or more substituents as set forth above;

"cycloalkynyl" refers to ring-containing alkynyl radicals having at least one carbon-carbon triple bond, and having in the range of about 3 up to 20 carbon atoms, and "substituted cycloalkynyl" refers to cyclic alkynyl radicals further bearing one or more substituents as set forth above;

"aryl" refers to mononuclear and polynuclear aromatic radicals having in the range of 6 up to 14 carbon atoms, and "substituted aryl" refers to aryl radicals further bearing one or more substituents as set forth above, for example, alkylaryl moieties;

"heterocycle" refers to ring-containing radicals having one or more heteroatoms (e.g., N, O, S) as part of the ring structure, and having in the range of about 3 up to 20 atoms in the ring. Heterocyclic moieties may be saturated or unsaturated when optionally containing one or more double bonds, and may contain more than one ring. Heterocyclic moieties include, for example, monocyclic moieties such as pyridyl moieties, piperidinyl moieties, imidazolyl moieties, pyrimidinyl moieties, isothiazolyl moieties, isoxazolyl moieties, dihydropyranyl moieties dihydrothiopyranyl moieties, pyranyl moieties, dioxinyl moieties, thienyl moieties, dithiolyl moieties, furyl moieties, furazanyl moieties and bicyclic heterocyclic moieties such as azabicycloalkanyl moieties and oxabicycloalkyl moieties. The term "substituted heterocycle" refers to heterocycles further bearing one or more substituents as set forth above;

"azo" refers to the bivalent moiety —N=N—, wherein each bond is attached to a different carbon atom;

"halogen" refers to fluoride, chloride, bromide or iodide radicals.

In accordance with the practice of the present invention, A is a 5-, 6- or 7-membered unsaturated heterocyclic moiety, containing a ring having at least one nitrogen atom located on the ring in a position adjacent to a carbon atom which bears a linking moiety as a substituent. The ring further contains 3, 4 or 5 independently variable atoms selected from carbon, nitrogen, sulfur and oxygen. Thus, A can be pyridinyl, imidazolyl, pyridazinyl, pyrimidinyl, pyrazinyl, triazolyl, triazinyl, tetrazolyl, tetrazinyl, isoxazolyl, oxazolyl, oxadiazolyl, oxatriazolyl, dioxazolyl, oxadiazinyl, isothiazolyl, thiazoyl, dioxazolyl, oxathiazolyl, oxathiazinyl, azepinyl, diazepinyl, and the like. Those of skill in the art will recognize that multiple isomers exist for a single chemical formula; each of the possible isomeric forms of the various empirical formulae set forth herein are contemplated by the invention. When a variable ring atom is carbon, it bears a hydrogen, or is optionally substituted with halogen, substituted or unsubstituted hydrocarbyl, substituted or unsubstituted aryl, thiol, nitro, carboxyl, ester, cyano, amine, amide, carboxamide, amidine, amido, sulfonamide, and the like.

In accordance with one embodiment of the compounds used in the practice of the invention, A is a 5-, 6- or 7-membered ring containing, as ring members, a nitrogen atom and a sulfur atom. Moieties contemplated for use include those wherein A is isothiazol-3-yl(1,2-thiazol-3-yl), thiazol-4-yl(1,3,-thiazol-4-yl), thiazol-2-yl( 1,3-thiazol-2-yl), 1,2-thiazin-3-yl, 1,3-thiazin-4-yl, 1,4-thiazin-3-yl, 1,3-thiazin-2-yl, thiazepinyl, and the like. Presently preferred moieties include those wherein A is isothiazol-3-yl(1,2-thiazol-3-yl), thiazol-4-yl(1,3-thiazol-4-yl) and thiazol-2-yl( 1,3-thiazol-2-yl).

In accordance with another embodiment of the compounds used in the practice of the invention, A is a 5-, 6- or 7-membered ring containing, as ring members, a nitrogen atom and an oxygen atom. Moieties contemplated by this embodiment of the invention include those wherein A is 1,2-oxazin-3-yl, 1,3-oxazin-4-yl, 1,4-oxazin-3-yl, 1,3-oxazin-2-yl, oxazol-2-yl, isoxazol-3-yl, oxazol-4-yl, oxazepinyl, and the like. Presently preferred moieties include those wherein A is oxazol-2-yl, isoxazol-3-yl and oxazol-4-yl.

In accordance with another embodiment of the compounds used in the practice of the invention, A is a 5-, 6-, or 7-membered ring containing as ring members two nitrogen atoms. Moieties contemplated by this embodiment of the invention include those wherein A is 3-pyridazinyl (1,2-diazin-3-yl), pyrimidin-4-yl(1,3-diazin-4-yl), pyrazin-3-yl (1,4-diazin-3-yl), pyrimidin-2-yl(1,3-diazin-2-yl), pyrazol-3-yl( 1,2-diazol-3-yl), 1,3-isodiazol-4-yl, 1,3-isodiazol-2-yl, diazepinyl, and the like. Presently preferred moieties include those wherein A is 3-pyridazinyl (1,2-diazin-3-yl), pyrimidin-4-yl(1,3-diazin-4-yl), pyrazin-3-yl(1,4-diazin-3-yl), pyrimidin-2-yl( 1,3-diazin-2-yl), 1,3-isodiazol-4-yl and 1,3-isodiazol-2-yl.

In accordance with still another embodiment compounds used in the practice of the invention, A is a 5-, 6-, or 7-membered ring containing, as ring members, three nitrogen atoms. Moieties contemplated by this embodiment of the invention include those wherein A is 1,2,3-triazin-4-yl, 1,2,4-triazin-6-yl, 1,2,4-triazin-3-yl, 1,2,4-triazin-5-yl, 1,3,5-triazin-2-yl, 1,2,3-triazol-4-yl, 1,2,4-triazol-3-yl, triazepinyl, and the like. Presently preferred moieties include those wherein A is 1,2,3-triazin-4-yl, 1,2,4-triazin-6-yl, 1,2,4-triazin-3-yl, 1,2,4-triazin-5-yl, 1,3,5-triazin-2-yl, 1,2,3-triazol-4-yl, 1,2,4-triazol-3-yl.

In accordance with still other compounds used in the practice of the invention, A is a 5-, 6-, or 7-membered ring containing, as ring members, four nitrogen atoms. Moieties contemplated for use in the practice of the invention include those wherein A is tetrazin-2-yl, tetrazin-3-yl, tetrazin-5-yl, tetrazolyl, tetrazepinyl, and the like. Presently preferred moieties include those wherein A is tetrazolyl.

In accordance with yet other embodiments of compounds used in the practice of the invention, A is a 5-, 6-, or 7-membered ring containing, as ring members, one sulfur atom and two nitrogen atoms. Moieties contemplated by this embodiment of the invention include those wherein A is 1,2,6-thiadiazin-3-yl, 1,2,5-thiadiazin-3-yl, 1,2,4-thiadiazin-3-yl, 1,2,5-thiadiazin-4-yl, 1,2,3-thiadiazin-4-yl, 1,3,4-thiadiazin-5-yl, 1,3,4-thiadiazin-2-yl, 1,2,4-thiadiazin-5-yl, 1,3,5-thiadiazin-4-yl, 1,3,5-thiadiazin-2-yl, 1,2,4-thiadiazol-3-yl, 1,2,3-thiadiazol-4-yl, 1,3,4-thiadiazol-2-yl, 1,2,5-thiadiazol-3-yl, 1,2,4-thiadiazol-5-yl, thiadiazepinyl, and the like. Presently preferred moieties include those wherein A is 1,2,4-thiadiazol-3-yl, 1,2,3-thiadiazol-4-yl, 1,3,4-thiadiazol-2-yl, 1,2,5-thiadiazol-3-yl and 1,2,4-thiadiazol-5-yl.

In accordance with yet another embodiment of compounds used in the practice of the invention, A is a 5-, 6-, or 7-membered ring containing, as ring members, one oxygen atom and two nitrogen atoms. Moieties contemplated by this embodiment of the invention include those wherein A is 1,2,6-oxadiazin-3-yl, 1,2,5-oxadiazin-3-yl, 1,2,4-oxadiazin-3-yl, 1,2,5-oxadiazin-4-yl, 1,2,3-oxadiazin-4-yl, 1,3,4-oxadiazin-5-yl, 1,3,4-oxadiazin-2-yl, 1,2,4-oxadiazin-5-yl, 1,3,5-oxadiazin-4-yl, 1,3,5-oxadiazin-2-yl, 1,2,4-oxadiazol-3-yl, 1,2,3-oxadiazol-4-yl, 1,3,4-oxadiazol-2-yl, 1,2,5-oxadiazol-3-yl, 1,2,4-oxadiazol-5-yl, oxadiazepinyl, and the like. Presently preferred moieties include those wherein A is 1,2,4-oxadiazol-3-yl, 1,2,3-oxadiazol-4-yl, 1,3,4-oxadiazol-2-yl, 1,2,5-oxadiazol-3-yl and 1,2,4-oxadiazol-5-yl.

In accordance with still another embodiment of compounds used in the practice of the invention, A is a 5-, 6-, or 7-membered ring containing as ring members, one up to six nitrogen atoms, and/or one up to six carbon atoms, and/or zero up to five sulfur atoms, and/or zero up to five oxygen atoms.

Further, in accordance with compounds used in the practice of the present invention, L is a linking moiety which links moieties A and B. L is selected from substituted or unsubstituted alkenylene moieties, alkynylene moieties or azo moieties. Presently preferred compounds of the invention are those wherein L is alkenylene or alkynylene moieties containing two carbon atoms, with alkynylene most preferred.

Further, in accordance with compounds used in the practice of the present invention, B is a moiety linked through bridging moiety L to moiety A. Radicals contemplated for use in the invention are those wherein B is substituted or unsubstituted hydrocarbyl, substituted or unsubstituted cyclohydrocarbyl, substituted or unsubstituted heterocycle, optionally containing one or more double bonds, substituted or unsubstituted aryl, and the like.

Presently preferred compounds used in the practice of the invention are those wherein B is a substituted or unsubstituted hydrocarbyl selected from substituted or unsubstituted alkyl moieties, alkenyl moieties, dialkenyl moieties, trialkenyl moieties, alkynyl moieties, alkadiynyl moieties, alkatriynyl moieties, alkenynyl moieties, alkadienynyl moieties, alkenediynyl moieties, and the like.

Further preferred compounds used in the practice of the invention are those wherein B is a substituted or unsubstituted cyclohydrocarbyl selected from substituted or unsubstituted cycloalkyl moieties, cycloalkenyl moieties, cycloalkadienyl moieties, cycloalkatrienyl moieties, cycloalkynyl moieties, cycloalkadiynyl moieties, bicyclic hydrocarbon moieties wherein two rings have two atoms in common, and the like. Especially preferred compounds are those wherein B is cycloalkyl and cycloalkenyl having in the range of 4 up to about 8 carbon atoms.

Still further preferred compounds used in the practice of the invention are those wherein B is a substituted or unsubstituted heterocycle, optionally containing one or more double bonds. Exemplary compounds include pyridyl, thiazolyl, furyl, pyranyl, thiopyranyl, piperidinyl, and the like. Also preferred are compounds wherein B is substituted or unsubstituted aryl. Especially preferred compounds are those wherein substituents are methyl, trifluoromethyl and fluoro and wherein B is 3,5-di-trifluoromethyl phenyl.

Those of skill in the art recognize that compounds used in the practice of the invention may contain one or more chiral centers, and thus can exist as racemic mixtures. For many applications, it is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions. Those of skill in the art will further recognize that compounds used in the practice of the invention may exist in polymorphic forms wherein a compound is capable of crystallizing in different forms. Suitable methods for identifying and separating polymorphisms are known in the art.

As used herein, with reference to compounds not embraced by the scope of the claims, esterified carboxy is, for example, lower alkoxycarbonyl, phenyl-lower alkoxycarbonyl or phenyl-lower alkoxycarbonyl substituted in the phenyl moiety by one or more substituents selected from lower alkyl, lower alkoxy, halo and halo-lower alkyl. Esterified carboxy-lower-alkoxy is, for example, lower alkoxycarbonyl-lower alkoxy. Amidated carboxy is, for example, unsubstituted or aliphatically substituted carbamoyl such as carbamoyl, N-lower alkylcarbamoyl, N,N-di-lower alkylcarbamoyl unsubstituted or lower alkyl-, lower alkoxy-, halo- and/or trifluoromethyl-substituted N-phenyl- or N-lower-alkyl-N-phenyl-carbamoyl.

As used herein, with reference to compounds not embraced by the scope of the claims, acyl is, for example, lower alkanoyl, lower alkenoyl or unsubstituted or lower alkyl-, lower alkoxy-, halo- and/or trifluoromethyl-substituted benzoyl. Acylamino is, for example, lower alkanoylamino, and N-acyl-N-lower alkylamino is, for example, N-lower alkanoyl-N-lower-alkylamino or unsubstituted or lower alkyl-, lower alkoxy-, halo- and/or trifluoromethyl-substituted benzoylamino.

As referred to in reference to compounds not embraced by the scope of the claims "lower" groups are understood to comprise up to and including seven carbon atoms. N-lower-alkyl-N-phenylcarbamoyl is, for example, N—$C_1$–$C_4$alkyl-N-phenylcarbamoyl, such as N-methyl, N-ethyl, N-propyl, N-isopropyl or N-butyl-N-phenylcarbamoyl.

As used herein, with reference to compounds not embraced by the scope of the claims, amino-lower alkyl is, for example, amino-$C_1$–$C_4$alkyl, preferably of the formula —$(CH_2)_n$—$NH_2$ in which n is 2 or 3, such as aminomethyl, 2-aminoethyl, 3-aminopropyl or 4-aminobutyl. Hydroxy-lower alkyl is, for example, hydroxy-$C_1$–$C_4$alkyl, such as hydroxymethyl, 2-hydroxy ethyl, 3-hydroxypropyl, 2-hydroxyisopropyl or 4-hydroxybutyl. Halo-lower alkyl is, for example, polyhalo-$C_1$–$C_4$alkyl, such as trifluoromethyl.

As used herein, with reference to compounds not embraced by the scope of the claims, lower alkoxy is, for example, $C_1$–$C_7$alkoxy, preferably $C_1$–$C_4$alkoxy, such as methoxy, ethoxy, propyloxy, isopropyloxy or butyloxy, but may also represent isobutyloxy, sec.butyloxy, tert.-butyloxy or a $C_5$–$C_7$alkoxy group, such as a pentyloxy, hexyloxy or heptyloxy group. amino-lower alkoxy is, for example, amino-$C_2$–$C_4$alkoxy preferably of the formula —O—$(CH_2)_n$—$NR_aR_b$ in which n is 2 or 3, such as 2-aminoethoxy, 3-aminopropyloxy or 4-aminobutyloxy. Carboxy-lower-alkoxy is, for example, carboxy-$C_1$–$C_4$alkoxy, such as carboxymethoxy, 2-carboxyethoxy, 3-carboxypropyloxy or 4-carboxybutyloxy. Lower alkanoyloxy is, for example, $C_1$–$C_7$alkanoyloxy, such as acetoxy, propionyloxy, butyryloxy, isobutyryloxy or pivaloyloxy. Halo-lower alkoxy is, for example, halo- or polyhalo-$C_1$–$C_7$alkoxy, preferably halo- or polyhalo-$C_1$–$C_4$alkoxy, such as halo- or polyhaloethoxy, halo- or polyhalopropyloxy or butyl-oxy, wherein "poly" refers, for example, to tri- or pentahalo, and "halo" denotes, for example, fluoro or chloro.

As used herein, with reference to compounds not embraced by the scope of the claims, lower alkylamino-lower alkoxy is, for example, $C_1$–$C_4$alkylamino-$C_2$–$C_4$alkoxy, preferably of the formula —O—$(CH_2)_n$—$NR_aR_b$ in which n is 2 or 3 and $R_a$ and $R_b$, independently of each other, denote lower alkyl groups as defined hereinbefore, such as methyl, ethyl, propyl or butyl. Lower alkylamino-lower alkyl is, for example, $C_1$–$C_4$alkylamino-$C_1$–$C_4$alkyl, preferably of the formula —$(CH_2)_n$—$NR_aR_b$ in which n is 2 or 3 and $R_a$ and $R_b$, independently of each other, denote lower alkyl groups as defined hereinbefore, such as methyl, ethyl, propyl or butyl. Di-lower alkylamino-lower alkyl is, for example, Di-$C_1$–$C_4$alkylamino-$C_1$–$C_4$alkyl, preferably of the formula —$(CH_2)_n$—$NR_aR_b$ in which n is 2 or 3 and $R_a$ and $R_b$, independently of each other, denote lower alkyl groups such as methyl, ethyl, propyl or butyl. Di-lower alkylamino-lower alkoxy is, for example, Di-$C_1$–$C_4$alkylamino-$C_2$–$C_4$alkoxy, preferably of the formula —O—$(CH_2)_n$—$NR_aR_b$ in which n is 2 or 3 and $R_a$ and $R_b$, independently of each other, denote lower alkyl groups as defined hereinbefore, such as methyl, ethyl, propyl or butyl.

As used herein, with reference to compounds not embraced by the scope of the claims, optionally hydroxy-substituted lower alkyleneamino-lower alkyl is, for example, unsubstituted or hydroxy-substituted 5- to 7-membered alkyleneamino-$C_1$–$C_4$alkyl, preferably of the formula —$(CH_2)_n$—$R_c$ in which n is 2 or 3 and $R_c$ pyrrolidino, hydroxypyrrolidino, piperidino, hydroxypiperidino, homopiperidino or hydroxyhomopiperidino. Furthermore, optionally hydroxy-substituted lower alkyleneamino-lower alkoxy is, for example, unsubstituted or hydroxy-substituted 5 to 7-membered alkyleneamino-$C_1$–$C_4$alkoxy, preferably of the formula —O—$(CH_2)_n$—$R_c$ in which n is 2 or 3 and $R_c$ pyrrolidino, hydroxypyrrolidino, piperidino, hydroxypiperidino, homopiperidino or hydroxyhomopiperidino.

In accordance with another embodiment of the invention, there are provided methods of modulating the activity of metabotropic glutamate receptors, said method comprising contacting metabotropic glutamate receptors with a concentration of a heterocylic compound as described above sufficient to modulate the activity of said metabotropic glutamate receptors.

As used herein, the phrase "metabotropic glutamate receptor" refers to a class of cell-surface receptors which participates in the G-protein-coupled response of cells to glutamatergic ligands. Three groups of metabotropic glutamate receptors, identified on the basis of amino acid sequence homology, transduction mechanism and binding selectivity are presently known and each group contains one or more types of receptors. For example, Group I includes metabotropic glutamate receptors 1 and 5 (mGluR1 and mGluR5), Group II includes metabotropic glutamate receptors 2 and 3 (mGluR2 and mGluR3) and Group III includes metabotropic glutamate receptors 4, 6, 7 and 8 (mGluR4, mGluR6, mGluR7 and mGluR8). Several subtypes of each mGluR type may be found; for example, subtypes of mGluR1 include mGluR1*a*, mGluR1*b* and mGluR1*c*.

In accordance with another embodiment of the invention, there are provided methods of treating a wide variety of disease conditions, said method comprising administering to a patient having a disease condition a therapeutically effective amount of at least one of the heterocyclic compounds described above.

As used herein, "treating" refers to inhibiting or arresting the development of a disease, disorder or condition and/or causing the reduction, remission, or regression of a disease, disorder or condition. Those of skill in the art will understand that various methodologies and assays may be used to assess the development of a disease, disorder or condition, and similarly, various methodologies and assays may be used to assess the reduction, remission or regression of a disease, disorder or condition.

Disease conditions contemplated for treatment in accordance with the invention include cerebral ischemia, chronic neurodegeneration, psychiatric disorders, schizophrenia, mood disorders, emotion disorders, disorders of extrapyramidal motor function, obesity, disorders of respiration, motor control and function, attention deficit disorders, concentration disorders, pain disorders, neurodegenerative disorders, epilepsy, convulsive disorders, eating disorders, sleep disorders, sexual disorders, circadian disorders, drug withdrawal, drug addiction, compulsive disorders, anxiety, panic disorders, depressive disorders, skin disorders, retinal ischemia, retinal degeneration, glaucoma, disorders associated with organ transplantation, asthma, ischemia, astrocytomas, and the like.

Disease conditions contemplated for treatment in accordance with the present invention further include diseases of the pulmonary system, diseases of the nervous system, diseases of the cardiovascular system, diseases of the gastrointestinal system, diseases of the endocrine system, diseases of the exocrine system, diseases of the skin, cancer, diseases of the ophthalmic system, and the like.

As used herein, "administering" refers to means for providing heterocyclic compounds and/or salts thereof, as described herein, to a patient, using oral, sublingual intravenous, subcutaneous, transcutaneous, intramuscular, intracutaneous, intrathecal, epidural, intraoccular, intracranial, inhalation, rectal, vaginal, and the like administration. Administration in the form of creams, lotions, tablets, capsules, pellets, dispersible powders, granules, suppositoiries, syrups, elixirs, lozenges, injectable solutions, sterile aqueous or non-aqueous solutions, suspensions or emulsions, patches, and the like, is also contemplated. The active ingredients may be compounded with non-toxic, pharmaceutically acceptable carriers including, glucose, lactose, gum acacia, gelatin, mannitol, starch paste, magnesium trisilicate, talc, corn starch, keratin, colloidal silica, potato starch, urea, dextrans, and the like.

For purposes of oral administration, tablets, capsules, troches, aqueous or oily suspensions, dispersible powders or granules, emulsions, hard or soft capsules, or syrups, elixirs and lozenges containing various excipients such as calcium carbonae, lactose, calcium phosphate, sodium phosphate, and the like may be employed along with various granulating and disintegrating agents such as corn starch, potato starch, alginic acid, and the like, together with binding agents such as gum tragacanth, corn starch, gelatin, acacia, and the like. Lubricating agents such as magnesium stearate, stearic acid, talc, and the like may also be added. Preparations intended for oral use may be prepared according to any methods known to the art for the manufacture of pharmaceutical preparations and such preparations may contain one or more agents selected from the group consisting of a sweetening agent such as sucrose, lactose, saccharin, and the lake, flavoring agents such as peppermint, oil of wintergreen, and the like, coloring agents and preserving agents in order to provide pharmaceutically palatable preparations. Preparations for oral use may also contain suitable carriers include emulsions, solutions, suspensions, syrups, and the like, optionally containing additives such as wetting agents, emulsifying and suspending agents, sweetening, flavoring and perfuming agents, and the like. Tablets may be uncoated or they may be coated by known techniques to delay disintegration and absorption in the gastrointestinal tract and thereby provide a sustained action over a longer period of time.

For the preparation of fluids for parenteral administration, suitable carriers include sterile aqueous or non-aqueous solutions, suspensions, or emulsions. For parenteral administration, solutions for the practice of the invention may comprise sterile aqueous saline solutions, or the corresponding water soluble pharmaceutically acceptable metal salts, as previously described. For parenteral administration, solutions of the compounds used in the practice of the invention may also comprise non-aqueous solutions, suspensions, emulsions, and the like. Examples of nonaqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

Aqueous solutions may also be suitable for intravenous, intramuscular, intrathecal, subcutaneous, and intraperitoneal injection. The sterile aqueous media employed are all readily obtainable by standard techniques well known to those skilled in the art. They may be sterilized, for example, by filtration through a bacteria-retaining filter, by incorporating sterilizing agents into the compositions, by irradiating the compositions, by heating the compositions, and the like. They can also be manufactured in the form of sterile water, or some other sterile medium capable of injection immediately before use.

Compounds contemplated for use in the practice of the present invention may also be administered in the form of suppositories for rectal or vaginal administration. These compositions may be prepared by mixing the drug with a suitable non-irritating excipient, such as cocoa butter, synthetic glyceride esters of polyethylene glycols, and the like, such materials being solid at ambient temperatures but liquify and/or dissolve in internal cavities to release the drug.

The preferred therapeutic compositions for inocula and dosage will vary with the clinical indication. Some variation in dosage will necessarily occur depending upon the condition of the patient being treated, and the physician will, in any event, determine the appropriate dose for the individual patient. The effective amount of compound per unit dose depends, among other things, on the body weight, physiology, and chosen inoculation regimen. A unit dose of compound refers to the weight of compound without the weight of carrier (when carrier is used).

The route of delivery compounds and compositions used for the practice of the invention is determined by the disease and the site where treatment is required. Since the pharmacokinetics and pharmacodynamics of the compounds and compositions described herein will vary somewhat, the most preferred method for achieving a therapeutic concentration in a tissue is to gradually escalate the dosage and monitor the clinical effects. The initial dose, for such an escalating dosage regimen of therapy, will depend upon the route of administration.

In accordance with invention methods, the medicinal preparation can be introduced parenterally, by dermal application, and the like, in any medicinal form or composition. It is used as a solitary agent of medication or in combination with other medicinal preparations. Single and multiple therapeutic dosage regimens may prove useful in therapeutic protocols.

As employed herein, the phrase "a therapeutically effective amount", when used in reference to invention methods employing heterocyclic compounds and pharmaceutically acceptable salts thereof, refers to a dose of compound sufficient to provide circulating concentrations high enough to impart a beneficial effect on the recipient thereof. The specific therapeutically effective dose level for any particular patient will depend upon a variety of factors including the disorder being treated, the severity of the disorder, the activity of the specific compound used, the route of administration, the rate of clearance of the specific compound, the duration of treatment, the drugs used in combination or coincident with the specific compound, the age, body weight, sex, diet and general health of the patient, and like factors well known in the medical arts and sciences. Dosage levels typically fall in the range of about 0.001 up to 100 mg/kg/day; with levels in the range of about 0.05 up to 10 mg/kg/day being preferred.

In still another embodiment of the invention, there are provided methods for preventing disease conditions in a subject at risk thereof, said method comprising administering to said subject a therapeutically effective amount of at least one of the heterocyclic compounds described above.

As used herein, the phrase "preventing disease conditions" refers to preventing a disease, disorder or condition from occurring in a subject who may be at risk for the disease, but has not yet been diagnosed as having the disease. Those of skill in the art will understand that a variety of methods may be used to determine a subject at risk for a disease, and that whether a subject is at risk for a disease will depend on a variety of factors known to those of skill in the art, including genetic make-up of the subject, age, body weight, sex, diet, general health, occupation, exposure to environmental conditions, marital status, and the like, of the subject.

Those of skill in the art can readily identify a variety of assays that can be used to assess the activity of excitatory amino acid receptors. For receptor species that activate a second messenger pathway, assays that measure receptor-activated changes in intracellular second messengers can be employed to monitor receptor activity. For example, inhibition of G-protein-coupled metabotropic glutamate receptors by antagonists can lead to inhibition of the glutamate-evoked increase in phosphatidylinositol (PI) hydrolysis, which can be assessed by measuring decreases in glutamate-stimulated products of PI hydrolysis. (See e.g., Berridge et al, (1982) *Biochem. J.* 206:587–5950; and Nakajima et al., *J. Biol. Chem.* 267:2437–2442 (1992) and Example 23.) Similarly, activation of excitatory amino acid receptors that leads to the release of intracellular calcium or changes in intracellular calcium concentration can also be used to assess excitatory amino acid receptor activity. Methods of detection of transient increases in intracellular calcium concentration are well known in the art. (See e.g., Ito et al., *J. Neurochem.* 56:531–540 (1991) and Example 22). Furthermore, for receptor species that mediate analgesia, assays that measure analgesic efficacy can be employed to monitor receptor activity (See Example 24).

The invention will now be described in greater detail by reference to the following non-limiting examples.

EXAMPLE 1

Preparation of
4-Methyl-2-[(E)-2-phenylethenyl]-1,3-oxazole

Cinnamamide (2.0 g, 14 mmol), chloroacetone (0.93 mL, 16 mmol), and $K_2CO_3$ (940 mg, 6.8 mmol) were combined under argon and the mixture was heated in a 120° C. oil bath. The reaction mixture solidified and stirring stopped upon heating. After 16 h, the cooled reaction mixture was quenched by the addition of water (20 mL) and then diluted with ethyl acetate (100 mL). The organic phase was dried over $Na_2SO_4$, filtered, and concentrated in vacuo. The crude product was purified by column chromatography eluting with 90:10 hexane:ethyl acetate. The product that was obtained (280 mg) showed some close running impurities by thin layer chromatography (TLC). The material was further purified by preparative TLC via multiple elutions with 95:5 hexane:ethyl acetate. Isolation of the middle of the main band afforded 4-methyl-2-[(E)-2-phenylethenyl]-1,3-oxazole (47.0 mg, 2% yield) as a yellow oil. $^1$H NMR (CDCl$_3$, 300 MHz) δ 7.53-7.32 (m, 7H), 6.91 (d, J=16.4 Hz, 1H), 2.21 (s, 3H). MS (ESI) 185.7 (M$^+$+H).

EXAMPLE 2

4-Methyl-2-[2-phenylethenyl]-1,3-thiazole

The title compound was prepared in several steps, with the preparation of key intermediate steps set forth herein as follows:

Preparation of Ethyl 4-methyl-1,3-thiazole-2-carboxylate: Ethyl thiooxamate (3.0 g, 22 mmol) was dissolved in ethanol (30 mL) under argon. Chloroacetone (1.8 mL, 22 mmol) was added and the resultant solution was heated at 80° C. for 16 h. The reaction mixture was concentrated in vacuo, adsorbed onto silica gel, and purified by column chromatography on silica gel eluting with 97:3, then 95:5 hexane:ethyl acetate to afford ethyl 4-methyl-1,3-thiazole-2-carboxylate (850 mg, 22% yield) as an oil. $^1$H NMR (CDCl$_3$, 300 MHz) 7.20 (s, 1H), 4.48 (q, J=7.1 Hz, 2H), 2.56 (s, 3H), 1.47 (s, 3H). MS (EI ionization) 171 (M$^+$).

Preparation of (4-Methyl-1,3-thiazol-2-yl)methanol: Ethyl 4-methyl-1,3thiazole-2-carboxylate (450 mg, 2.6 mmol) was dissolved under argon in tetrahydrofuran (THF) (5 mL). The solution was cooled to 0° C. in an ice bath and treated with diisobutylaluminum hydride (5.3 mL of a 1.5M solution in toluene, 7.9 mmol). The reaction mixture was allowed to slowly warm to ambient temperature over 16 h and then cooled to −78° C. and cautiously quenched by the dropwise addition of methanol. After gas evolution had ceased, saturated aqueous sodium-potassium tartrate (10 mL) was added, and the reaction mixture was allowed to warm to ambient temperature. The aqueous phase was extracted with ethyl acetate (3×30 mL), the combined organics dried over Na$_2$SO$_4$, filtered, and concentrated in vacuo. The crude product was purified by column chromatography on silica gel eluting with 90:10 then 1:1 hexane:ethyl acetate to afford (4-methyl-1,3-thiazol-2-yl)methanol (180 mg, 53% yield) as an oil. $^1$H NMR (CDCl$_3$, 300 MHz)δ 6.81 (s, 1H), 4.84 (s, 3H), 2.36 (s, 3H). MS (EI ionization) 129 (M$^+$).

Preparation of 4-Methyl-1,3-thiazole-2-carbaldehyde: (4-Methyl-1,3thiazol-2-yl)methanol (180 mg, 1.4 mmol) was dissolved in CH$_2$Cl$_2$ (9 mL), and treated with Magtrieve™(2.5 g). The resultant suspension was heated to reflux for 16 h. The reaction mixture was cooled and filtered through a pad of Celite™. The filter pad was washed thoroughly with CH$_2$Cl$_2$ and the combined filtrates were concentrated in vacuo to afford 4-methyl-1,3-thiazole-2-carbaldehyde (120 mg, 67% yield) as an oil. The material was carried on to the next step without further purification. MS (EI ionization) 127 (M$^+$).

Preparation of 4-Methyl-2-[2-phenylethenyl]-1,3-thiazole: Sodium hydride (102 mg of a 60% suspension in mineral oil, 4.3 mmol) was slurried in dry 1,2-dimethoxyethane (DME) under argon, cooled to 0° C. in an ice bath, and diethylbenzyl phosphonate (0.89 mL, 4.3 mmol) was added dropwise to the suspension. Thirty minutes after the completion of the phosphonate addition, 4-methylthiazole-2-carboxaldehyde (120 mg, 0.94 mmol) was added as a solution in DME (5 mL). After stirring for 4 h, further NaH (40 mg of a 60% suspension in mineral oil, 1.0 mmol) was added and the reaction mixture was allowed to warm to ambient temperature and stir for 16 h. The reaction mixture was quenched by the addition of water (20 mL) and ethyl acetate (50 mL). The aqueous phase was extracted with ethyl acetate (2×30 mL), the combined organics were dried over Na$_2$SO$_4$, filtered, and concentrated in vacuo. The crude product was purified by column chromatography on silica gel eluting with 90:10 hexane:ethyl acetate to afford 4-methyl-2-[2-phenylethenyl]-1,3-thiazole (30 mg, 16% yield) as an oil. $^1$H NMR analysis showed the material to be a 10:1 mixture of E and Z isomers (spectral data are reported for the major isomer). $^1$H NMR (CDCl$_{3,300}$ MHz) δ: 7.54-7.51 (m, 2H) 7.42-7.23 (m, 5H) 6.80 (s, 1H) 2.47 (s, 3H). MS (ESI) (minor isomer) 202.2 (M$^+$+H), (major isomer) 201.6 (M$^+$).

EXAMPLE 3

2-Methyl-4-[(E)-2-phenylethenyl]-1,3-thiazole

The title compound was prepared in several steps, with the preparation of key intermediate steps set forth herein as follows:

Preparation of Ethyl 2-methyl-1,3-thiazole-4-carboxylate: Thioacetamide (7.6 g, 100 mmol) was added to ethanol (60 mL), and the resultant suspension was cooled to 0° C. and treated with ethyl bromopyruvate (12.5 mL, 100 mmol). The resultant solution was stirred for five minutes at 0° C. at which time the ice bath was removed and the solution was allowed to warm to ambient temperature. After 0.5 h at ambient temperature, the solution was heated to reflux. After 12 h, the solvents were removed in vacuo, and the resultant crude product was taken up in ethyl acetate (300 mL). The organic phase was washed with saturated aqueous NaHCO$_3$ (50 mL), and the basic aqueous solution was then extracted with additionalethyl acetate (2×50 mL). The combined organic solutions were washed with brine (50 mL), dried over Na$_2$SO$_4$ and filtered. The filtrate was concentrated in vacuo to afford a yellow waxy solid. The crude product was dissolved in a small amount of hot ethyl acetate, diluted with hot hexane, and the resultant solution was allowed to cool to ambient temperature, seeded with a small amount of crude product, and transferred to the freezer. After 16 h the crystalline product was collected, washed with cold 8:1 hexane:ethyl acetate, and allowed to dry under high vacuum to afford ethyl 2-methyl-1,3-thiazole-4-carboxylate (11.76 g, 69% yield) as large brownish crystals. M.p. 56–58.5° C. 1H NMR (CDCl3, 300 MHz) δ 8.06 (s, 1H), 4.43 (q, 2H), 2.78 (s, 3H), 1.42 (t, 3H). MS (EI ionization) 171 (M+).

Preparation of (2-Methyl-1,3-thiazol-4-yl)methanol: Ethyl 2-methyl-1,3-thiazole-4-carboxylate (15 g, 60 mmol) was slurried in THF (40 mL) and cooled to 0° C. Lithium aluminum hydride (60 mL of a 1M solution in THF) was added slowly and the reaction mixture was allowed to warm to 25° C. After 16 h the reaction was quenched by the dropwise addition of water (2.28 mL), 15% NaOH solution (2.28 mL) and then water (6.84 mL). Ethyl acetate (100 mL) was added, the reaction mixture filtered, and the filtrate concentrated in vacuo. The crude residue was chromatographed on silica gel with ethyl acetate:hexane (1:1) as eluant to afford (2-methyl-1,3-thiazol-4-yl)methanol as an oil (4.41 g, 57%). This material was carried on to the next step without further purification.

Preparation of 2-Methyl-1,3-thiazole-4-carbaldehyde: (2-Methyl-1,3-thiazol-4-yl)methanol (4.4 g, 34 mmol) was dissolved in CH$_2$Cl$_2$ (400 mL). Magtrieve™(44 g) was added and the reaction was heated under reflux for 24 h. The mixture was filtered through Celite™, and the filter pad was washed thoroughly with CH$_2$Cl$_2$. The filtrate was concentrated in vacuo to afford 2-methyl-1,3-thiazole-4-carbaldehyde (3.7g, 86% yield) as a yellow oil which was carried on to the next step without further purification. 1H NMR (CDCl3, 300 MHz) δ 9.98 (s, 1H), 8.06 (s, 1H,), 2.79 (s, 3H,). MS (EI ionization) 127 (M+).

Preparation of 2-Methyl-4-[(E)-2-phenylethenyl]-1,3-thiazole: Sodium hydride (120 mg of a 60% suspension in mineral oil, 3.0 mmol) was slurried in DME (6 mL) and cooled to 0° C. Diethyl benzylphosphonate (1.1 g, 5.0 mmol) was added dropwise and after 15 minutes, 2-methyl-1,3-thiazole-4-carbaldehyde (320 mg, 2.5 mmol) in DME (5 mL) was added dropwise to the reaction mixture. After 3 h at 0° C. the reaction mixture was diluted with ethyl acetate (10 mL) and washed with saturated aqueous NH$_4$Cl (10 mL), saturated aqueous NaHCO$_3$ (10 mL), brine (10 mL), dried over Na$_2$SO$_4$, filtered, and concentrated in vacuo. The crude product was purified by column chromatography on silica gel eluting with 90:10 hexane:ethyl acetate to afford 2-methyl-4-[(E)-2-phenylethenyl]-1,3-thiazole (330 mg, 65% yield) as an oil. 1H NMR (CDCl3, 300 MHz) δ 7–7.5 (m, 8H), 2.7 (s, 3H). MS (ESI) 202.1 (M++H).

EXAMPLE 4

2-Methyl-4-(phenylethynyl)-1,3-thiazole, p-toluenesulfonic acid salt

The title compound was prepared in several steps, with the preparation of key intermediate steps set forth herein as follows:

Preparation of 1-Chloro-4-phenyl-3-butyn-2-one: Anhydrous ZnCl$_2$ (10 g, 73 mmol) was dissolved in THF (50 mL) and the solution cooled to 0° C. in an ice bath. In another flask phenylacetylene (8.0 mL, 73 mmol) was dissolved in THF (50 mL), cooled to 0° C. in an ice bath, and treated with n-butyllithium (32 mL of a 2.2M solution in hexane, 70 mmol). After 20 minutes the phenylethynyllithium solution was added via cannula to the ZnCl$_2$ solution. After an additional 20 minutes Pd(PPh$_3$)$_4$ (1.23 g, 1.06 mmol) was added to the alkynylzinc solution. The resulting yellow solution was treated with chloroacetyl chloride (8.8 mL, 110 mmol) dropwise over 10 minutes. After 2 h at 0° C. the reaction mixture was quenched by the addition of cold aqueous 1M HCl (50 mL), and diethyl ether (500 mL). The acidic aqueous was extracted with diethyl ether (2×50 mL) and the combined organic extracts were washed with water (50 mL), saturated NaHCO$_3$ (50 mL), and brine (50 mL). The dark solution was dried and decolorized over Na$_2$SO$_4$ and charcoal and filtered through a pad of Celite™. The pad was washed thoroughly with ethyl acetate and the combined filtrates were concentrated in vacuo to afford a dark brown oil. The crude product was purified by column chromatography eluting with hexane, 99:1, 98:2, 96:4, then 94:6 hexane:ethyl acetate to afford 1-chloro-4-phenyl-3-butyn-2-one (7.83 g, 60% yield) as an orange oil which darkened and partially solidified upon standing in the freezer. 1H NMR (CDCl3, 300 MHz) δ 7.63–7.60 (m, 2H), 7.53–7.39 (m, 3H), 4.33 (s, 3H). MS (EI ionization) 178 (35Cl M+), 180 (37Cl M+).

Preparation of 2-Methyl-4-(phenylethynyl)-1,3-thiazole, p-toluenesulfonic acid salt: 1-Chloro-4-phenyl-3-butyn-2-one (1.6 g, 9.1 mmol) was dissolved in dry acetonitrile (15 mL), treated with thioacetamide (680 mg, 9.1 mmol), and heated to reflux for 4 h. After cooling, the acetonitrile was removed in vacuo, and the residue was partitioned between water (50 mL) and ethyl acetate (150 mL). The organic phase was dried over Na$_2$SO$_4$, filtered, concentrated in vacuo, adsorbed onto silica gel, and purified by column chromatography on silica gel eluting with 99:1, 98:2, then 95:5 hexane:ethyl acetate to afford 2-methyl-4-(phenylethynyl)-1,3-thiazole (240 mg, 13% yield) as a red oil. 1H NMR (CDCl3, 300 MHz) δ 7.58–7.54 (m, 2H), 7.40–7.34 (m, 4H), 2.74 (s, 3H). MS (EI ionization) 199 (M+).

2-Methyl-4-(phenylethynyl)-1,3-thiazole (270 mg, 1.35 mmol) was dissolved in ethanol (6 mL) at ambient temperature. p-Toluenesulfonic acid monohydrate (252 mg, 1.32 mmol) was added in one portion to afford a brown solution. After all of the acid had dissolved the reaction mixture was stirred for several minutes and then concentrated in vacuo to afford a dark brown oil which partially solidified under high vacuum. The crude material was triturated with diethyl ether, and the resulting solids were taken up in hot ethyl acetate. The hot solution was treated with decolorizing carbon and filtered hot to afford a pale brown solution, which was treated with hexane until cloudy, then heated to afford a clear solution. The solution was seeded with authentic product and allowed to crystallize. After cooling to ambient temperature the material was stored in the freezer for 16 h. The supernatant solution was decanted and the crystalline solids were pumped down under high vacuum to afford crystalline 2-methyl-4-(phenylethynyl)-1,3-thiazole, p-toluenesulfonic acid salt (260 mg, 52% yield) as brown crystals. M.p. 131–132.5° C. 1H NMR (CD3OD, 300 MHz) δ 7.99 (s, 1H), 7.70 (d, J=8.1 Hz), 7.60–7.57 (m, 2H), 7.46–7.43 (m, 3H), 7.23 (d, J=8 Hz, 2H), 2.89, (s, 3H), 2.36 (s, 3H). MS (ESI) 199.7 (M++H).

EXAMPLE 5

Preparation of 4-(Phenylethynyl)-1,3-thiazol-2-amine, p-toluenesulfonic acid salt 1-Chloro-4-phenyl-3-butyn-2-one (245 mg, 1.37 mmol) was dissolved in DMF (1.0 mL), thiourea (126 mg, 1.66 mmol) was added, and the resulting pale brown solution was stirred at ambient temperature for 5 days. The reaction mixture was diluted with Ethyl acetate (50 mL), washed with saturated NaHCO$_3$ solution (10 mL), water (10 mL), brine (10 mL), dried over Na$_2$SO$_4$, filtered, and concentrated in vacuo. The dark oil was dissolved in methanol, adsorbed onto silica gel and purified by column chromatography eluting with 4:1, 3:1, then 2:1 hexane:ethyl acetate to afford 4-(phenylethynyl)-1,3-thiazol-2-amine (56 mg, 20% yield) as an oil. 1H NMR (CDCl3, 300 MHz) δ 7.53–7.50 (m, 2H), 7.37–7.32 (m, 3H), 6.77 (s, 1H), 5.41 (br s, 2H). MS (EI ionization) 200 (M+).

4-(Phenylethynyl)-1,3-thiazol-2-amine (700 mg, 3.5 mmol) was dissolved in ethanol (20 mL) at ambient temperature. p-Toluenesulfonic acid monohydrate (660 mg, 3.5 mmol) was added in one portion to afford a brown solution. After all of the acid had dissolved the reaction mixture was stirred for several minutes and then concentrated in vacuo to afford a dark brown oil which solidified under high vacuum. The crude material was dissolved in hot ethyl acetate containing a few drops of methanol. After cooling to ambient temperature the material was stored in the freezer for few hours. The supernatant solution was decanted and the crystalline solids were dried under high vacuum to afford crystalline 4-(phenylethynyl)-1,3-thiazol-2-amine, p-toluenesulfonic acid salt (1.0 g, 73% yield) as brown crystals. M.p. 131–132.5° C. 1H NMR (CD$_3$OD, 300 MHz) δ 7.73–7.70 (d, J=9 Hz, 2H), 7.56–7.52 (dd, J=9, 2 Hz, 2H), 7.48–7.37 (m, 3H), 7.23–7.20 (d, J=9 Hz, 2H), 7.12, (s, 1H), 2.34 (s, 3H).

EXAMPLE 6

4-Methyl-5-(phenylethynyl)-1,3-thiazole

The title compound was prepared in several steps, with the preparation of key intermediate steps set forth herein as follows:

Preparation of 5-Bromo-4-methyl-1,3-thiazole: N-Bromosuccinimide (30 g, 170 mmol) was suspended in $CCl_4$ (150 mL) and 4-methylthiazole (15 g, 150 mmol) was added in one portion. The mixture was heated under reflux for 4 h then allowed to cool to ambient temperature. The reaction mixture was diluted with ethyl acetate (500 mL) and washed with water, then brine. The organics were dried over $Na_2SO_4$, filtered and concentrated in vacuo. The residue was purified by column chromatography eluting with 9:1 hexane:methylene chloride to afford 5-bromo-4-methyl-1,3-thiazole (6.8g, 24% yield) as a dark reddish oil. 1H NMR (CDCl3, 300 MHz) δ 8.69 (s, 1H), 2.44 (s, 3H). MS (EI ionization) 177 (35Cl M+), 179 (37Cl M+).

Preparation of 4-Methyl-5-(phenylethynyl)-1,3-thiazole: 5-Bromo-4-methyl-1,3-thiazole (570 mg, 3.2 mmol) and CuI (120 mg, 0.63 mmol) were combined in DME (5 mL) and argon gas was bubbled through the suspension for several minutes to deoxygenate the mixture. Triethylamine (2.0 mL, 14 mmol) and $PdCl_2(PPh_3)_2$ (220 mg, 0.32 mmol) were added, followed by the dropwise addition of phenylacetylene (1.0 mL, 9.5 mmol). After 16 h stirring at ambient temperature additional phenylacetylene (0.35 mL, 3.2 mmol), CuI, (61 mg, 0.32 mmol), and $PdCl_2(PPh_3)_2$ (110 mg, 0.16 mmol) were added and the reaction mixture was stirred for a further 16 h. The reaction was then heated to reflux, and after 3 h the reaction mixture was cooled, diluted with ethyl acetate (20 mL), and filtered through Celite™. The filter pad was washed thoroughly with ethyl acetate and the combined filtrates were washed with water (20 mL), brine (20 mL), dried over $Na_2SO_4$, filtered and concentrated in vacuo. The residue was purified by column chromatography on silica gel eluting with 95:5 hexane:ethyl acetate to afford 4-methyl-5-(phenylethynyl)-1,3-thiazole (166 mg, 26% yield) as a red oil. 1H NMR (CDCl3, 300 MHz) δ 8.62 (s, 1H), 7.54–7.50 (m, 2H), 7.37–7.26 (m, 3H), 2.6 (s, 3H). MS (ESI) 200.1 (M++H).

EXAMPLE 7

5-[(2-Fluorophenyl)ethynyl]-4-methyl-1,3-thiazole

5-Bromo-4-methyl-1,3-thiazole (500 mg, 2.8 mmol) and CuI (120 mg, 0.63 mmol) were combined in DME (5 mL) and argon gas was bubbled through the suspension for several minutes to deoxygenate the mixture. Triethylamine (2.0 mL, 14 mmol) and $PdCl_2(PPh_3)_2$ (220 mg, 0.32 mmol) were added, followed by the dropwise addition of (2-fluorophenyl)acetylene (1.0 g, 8.3 mmol). The reaction mixture was heated and after 3 h at reflux, allowed to cool, diluted with ethyl acetate (20 mL), and filtered through Celite™. The filter pad was washed thoroughly with ethyl acetate and the combined filtrates were washed with water (20 mL), brine (20 mL), dried over $Na_2SO_4$, and filtered. The filtrate was concentrated in vacuo, and the residue was purified by column chromatography on silica gel eluting with 95:5 hexane:ethyl acetate to afford 5-[(2-fluorophenyl)ethynyl]-4-methyl-1,3-thiazole (690 mg, 56% yield) as a red oil. 1H NMR (CDCl3, 300 MHz) δ 8.65 (s, 1H), 7.53–7.47 (m, 1H), 7.36–7.26 (m, 1H), 7.17–7.09 (m, 2H), 2.62 (s, 3H). MS (ESI) 217.3 (M+).

EXAMPLE 8

2-(Phenylethynyl)-1,3-thiazole, p-toluenesulfonic acid salt

2-Bromo-1,3-thiazole (2.0 g, 12 mmol) and CuI (460 mg, 2.4 mmol) were combined in DME (40 mL), and argon gas was bubbled through the suspension for several minutes to deoxygenate the mixture. Triethylamine (8.6 mL, 62 mmol) and PdCl2(PPh3)2 (856 mg, 1.22 mmol) were added and then phenylacetylene (3.7g, 36.5 mmol) was added dropwise. The reaction was heated to reflux at which point the reaction mixture solidified. Additional DME (20 mL) was added to dissolve the solids and the reaction mixture was allowed to stir for 16 h at reflux, at which time GC/MS showed no remaining 2-bromothiazole. After cooling, the mixture was diluted with 200 mL ethyl acetate, and filtered through Celite™. The pad was then washed thoroughly with ethyl acetate and the combined filtrates were washed with water (200 mL), brine (200 mL), dried over $Na_2SO_4$, and filtered. The filtrate was concentrated in vacuo, and the residue was purified by column chromatography eluting with hexane, then 97:3 hexane:ethyl acetate) to afford 2-(phenylethynyl)-1,3-thiazole (1.3 g, 60% yield) as a yellowish oil. 1H NMR (CDCl3, 300 MHz) δ 7.86 (d, J=3.2 Hz, 1H), 7.61–7.57 (m, 2H), 7.42–7.26 (m, 4H). MS (ESI) 185.2 (M+).

2-(Phenylethynyl)-1,3-thiazole (3.00 g, 16.2 mmol) was dissolved in ethanol (75 mL) at ambient temperature. p-Toluenesulfonic acid monohydrate (3.08 g, 16.2 mmol) was added in one portion to afford a yellow solution. After all of the acid had dissolved the reaction mixture was stirred for several minutes and then concentrated in vacuo to afford a bright yellow solid. An attempt was made to recrystallize the material from hot ethyl acetate:hexane, but the recovery of solid after cooling was poor. Analysis of the crude material from the reaction showed it to be of sufficient purity. 2-(Phenylethynyl)-1,3-thiazole, p-toluenesulfonic acid salt (4.77 g, 82% yield) was obtained as a bright yellow powder that turns beige upon standing at ambient temperature. M.p. 130–132° C. 1H NMR (CD3OD, 300 MHz) δ 8.17 (d, J=3.7 Hz, 1H), 8.05 (d, J=3.7 Hz, 1H), 7.72–7.67 (m, 4H), 7.56–7.46 (m, 3H), 7.22 (d, J=8 Hz, 2H), 2.35 (s, 3H). MS (ESI) 186.1 (M++H).

EXAMPLE 9

4-Bromo-2-(phenylethynyl)-1.3-thiazole 2,4-Dibromo-1,3-thiazole (2.0 g, 8.2 mmol) and CuI (312 mg, 1.64 mmol) were combined in DME (25 mL) and argon gas was bubbled through the suspension for several minutes to deoxygenate the mixture. Triethylamine (5.7 mL, 41 mmol) and $PdCl_2(PPh_3)_2$ (580 mg, 0.82 mmol) were added, and then phenylacetylene (0.90 mL, 8.6 mmol) was added dropwise. The reaction was stirred for 4 h at ambient temperature at which point GC/MS analysis showed the reaction to be complete. The mixture was filtered through Celite™, the filter pad was washed thoroughly with Ethyl acetate and the combined filtrates were then concentrated in vacuo. The residue was dissolved in ethyl acetate (200 mL), washed with water (200 mL), brine (200 mL), dried over $Na_2SO_4$, filtered and concentrated in vacuo. The residue was purified by column chromatography eluting with hexane, then 97:3 hexane:ethyl acetate to afford pure 4-bromo-2-(phenylethynyl)-1,3-thiazole (1.0 g, 46% yield) as a colorless solid. M.p. 79–82° C.; 1H NMR (CDCl3, 300 MHz) δ

7.60–7.56 (m, 2H) 7.45–7.26 (m, 3H), 7.26 (s, 1H). MS (EI ionization) 263 (M+, 79Br), 265 (M+, 81Br).

EXAMPLE 10

5-Methyl-2-(phenylethynyl)-1,3-thiazole

4-Bromo-2-(phenylethynyl)-1,3-thiazole (500 mg, 1.89 mmol) was dissolved in dry THF (10 mL) under argon, cooled to −78° C., then t-butyllithium (1.7 mL of a 1.7M solution in pentane, 2.8 mmol) was added. After 30 min 0.4 mL of the reaction mixture was quenched with saturated $NH_4Cl$ and extracted with ethyl acetate. GC/MS of the crude product from this workup and comparison with a GC/MS of authentic 2-(2-phenylethynyl)-thiazole showed the two to be identical. This confirmed that the initial coupling with phenylacetylene (in Example 9) took place at the bromine at the 2 position rather than at the 4 position. The GC/MS also showed that the reaction was not complete. Additional t-butyllithium (1.7 mL of a 1.7M solution in pentane, 2.8 mmol) was added. After 30 minutes iodomethane (0.36 mL, 5.7 mmol) was added to the reaction mixture, and the reaction was allowed to warm to ambient temperature for 16 h. The solvents were then removed in vacuo, and residue dissolved in ethyl acetate (50 mL), washed with water (50 mL), brine (50 mL), dried over $Na_2SO_4$, filtered, and concentrated in vacuo. The crude product was purified by column chromatography eluting with hexane, 99:1, 98:2, 97.5:2.5 hexane:ethyl acetate to afford 2-(2-phenylethynyl)-5-methyl-1,3-thiazole (90 mg). 1H NMR analysis of the material showed it to be impure, despite its apparent homogeneity by TLC analysis. The crude compound was dissolved in DMSO and purified by preparative HPLC with a 30 min gradient from 70:30 water:acetonitrile to 100% acetonitrile to afford pure 5-methyl-2-(phenylethynyl)-1,3-thiazole as a white powder (44 mg, 24% yield). M.p. 82–83° C. 1H NMR (CDCl3, 300 MHz) δ 7.85–7.55 (m, 2H), 7.49 (d, J=0.6 Hz, 1H), 7.37–7.32 (m, 3H), 2.49 (s, 3H). MS (ESI) 200.1 (M++H).

EXAMPLE 11

2-[(3-Methylphenyl)ethynyl]-1.3-thiazole

2-Bromo-1,3-thiazole (2.0 g, 13 mmol) and CuI (330 mg, 1.7 mmol) were combined in DME (25 mL) and argon gas was bubbled through the suspension for several minutes to deoxygenate the mixture. Triethylamine (5.7 mL, 43 mmol) and $PdCl_2(PPh_3)_2$ (604 mg, 0.86 mmol) were added and m-tolylacetylene (1.0 g, 8.6 mmol) was added dropwise. The reaction mixture was heated under reflux for 4 h at which time GC/MS showed the reaction was complete. The mixture was filtered through Celite™, and the filter pad was washed thoroughly with ethyl acetate. The combined filtrates were concentrated in vacuo. The residue was dissolved in ethyl acetate (200 mL), washed with water (200 mL), brine (200 mL), dried over $Na_2SO_4$, filtered and concentrated in vacuo. The residue was purified by column chromatography eluting with hexane then 98:2 hexane:ethyl acetate to afford 2-[2-(3-methylphenyl)ethynyl]-thiazole (280 mg, 16% yield) as a yellow oil which was still impure by 1H NMR analysis. The compound (280 mg) was dissolved in DMSO and purified by preparative HPLC with a 30 min gradient from 70:30 water:acetonitrile to 100% acetonitrile to afford pure 2-[(3-methylphenyl)ethynyl]-1,3-thiazole (122 mg, 6% yield) as a yellow oil. 1H NMR (CDCl3, 300 MHz) δ 7.84 (d, J=3.0 Hz, 1H), 7.40–7.34 (m, 3H), 7.28–7.18 (m, 2H), 2.34 (s, 3H). MS (ESI) 200.1 (M++H).

EXAMPLE 12

2-[(4-Fluorophenyl)ethynyl]-1,3-thiazole

2-Bromo-1,3-thiazole (1.0 g, 6.2 mmol) and CuI (152.4 mg, 0.8 mmol) were combined in DME (17 mL) and argon gas was bubbled through the suspension for several minutes to deoxygenate the mixture. Triethylamine (3 mL, 21 mmol) and $PdCl_2(PPh_3)_2$ (280 mg, 0.40 mmol) were added and 1-ethynyl-4-fluorobenzene (500 mg, 4.2 mmol) was added dropwise. The reaction was heated under reflux for 4 h at which time GC/MS showed the reaction was complete. The mixture was filtered through Celite™, and the filter pad was washed thoroughly with Ethyl acetate. The combined filtrates were then concentrated in vacuo. The residue was dissolved in ethyl acetate (100 mL), washed with water (100 mL), brine (100 mL), dried over $Na_2SO_4$, filtered and concentrated in vacuo. The residue was purified by column chromatography eluting with hexane then 98:2 hexane:ethyl acetate to 2-[(4-fluorophenyl)ethynyl]-1,3-thiazole as a white solid which was impure by 1H NMR analysis. The compound (280 mg) was dissolved in DMSO and purified by preparative HPLC with a 30 min gradient from 60:40 water:acetonitrile to 100% acetonitrile to afford 2-[(4-fluorophenyl)ethynyl]-1,3-thiazole (33 mg, 3% yield) as a white solid. M.p. 78–79° C. 1H NMR (CDCl3, 300 MHz) δ 7.83 (d, J=3.0 Hz, 1H), 7.60–7.55(m, 2H), 7.39 (d, J=3.0 Hz, 1H), 7.14–7.00 (m, 2H). MS (ESI) 204 (M⁺+H).

EXAMPLE 13

2-[(2-Fluorophenyl)ethynyl]-1,3-thiazole

2-Bromo-1,3-thiazole (2.0 g, 13 mmol) and CuI (316 mg, 1.6 mmol) were combined in DME (25 mL) and argon gas was bubbled through the suspension for several minutes to deoxygenate the mixture. Triethylamine (5.8 mL, 42 mmol) and $PdCl_2(PPh_3)_2$ (580 mg, 0.83 mmol) were added and 1-ethynyl-2-fluorobenzene (1.0 g, 8.3 mmol) was added dropwise. The reaction was heated under reflux for 4 h at which time GC/MS showed the reaction was complete. The mixture was filtered through Celite™, and the filter pad was washed thoroughly with ethyl acetate. The combined filtrates were concentrated in vacuo. The residue was dissolved in ethyl acetate (200 mL) and washed with water (200 mL), brine (200 mL), dried over $Na_2SO_4$, filtered and concentrated in vacuo. The residue was purified by column chromatography eluting with hexane then 98:2 hexane:ethyl acetate to afford 2-[(2-fluorophenyl)ethynyl]-1,3-thiazole (700 mg, 41% yield) as a yellow oil that was impure by 1H NMR analysis. The compound (140 mg) was dissolved in DMSO and purified by preparative HPLC with a 30 min gradient from 50:50 water:acetonitrile to 100% acetonitrile to afford 2-[(2-fluorophenyl)ethynyl]-1,3-thiazole (53.2 mg, 75% yield) as a yellow oil. 1H NMR (CDCl₃, 300 MHz) δ 7.88 (d, J=3.0 Hz, 1H), 7.59–7.53 (m, 1H), 7.42–7.35 (m, 2H), 7.18–7.09 (m, 2H). MS (ESI) 204 (M⁺+H).

EXAMPLE 14

4,5-Dimethyl-2-(phenylethynyl)-1,3-thiazole.

The title compound was prepared in several steps, with the preparation of key intermediate steps set forth herein as follows:

Preparation of 2-Bromo-4,5-dimethyl-1,3-thiazole: 4,5-Dimethyl-1,3-thiazole (5.0 g, 44 mmol) was dissolved in carbon tetrachloride (60 mL), and N-bromosuccinimide (8.19 g, 46 mmol) was added. The resulting mixture was heated to reflux while protected from light with aluminum foil. After ½ h at reflux the dark suspension was cooled and allowed to stand at ambient temperature for 16 h. The reaction mixture was then heated to reflux for an additional 4 h and cooled to ambient temperature. After standing at ambient temperature for 16 h, GC/MS analysis showed mostly monobromide, with a small amount of starting 4,5-dimethyl-1,3-thiazole present. The yellow supernatant solution was decanted from the black solids that had deposited on the walls of the flask. The crude product was concentrated in vacuo, and then further purified by column chromatography eluting with hexane, 99:1, 98:2, 96:4, 94:6, then 90:10 hexane:ethyl acetate to afford 2-bromo-4,5-dimethyl-1,3-thiazole (1.34 g, 16% yield) as a white semi-solid. M.p. 55–60° C. $^1$H NMR (CDCl$_3$, 300 MHz) δ 2.31 (s, 3H), 2.30 (s, 3H). MS (EI ionization) 191 (M$^+$, $^{79}$Br), 193 (M$^+$, $^{81}$Br).

Preparation 4,5-Dimethyl-2-(phenylethynyl)-1,3-thiazole: 2-Bromo-4,5-dimethyl-1,3-thiazole (1.3 g, 6.8 mmol) and CuI (190 mg, 1.36 mmol) were combined in DME (30 mL) and argon gas was bubbled through the suspension for several minutes to deoxygenate the mixture. Triethylamine (5.0 mL, 34 mmol) and PdCl2(PPh3)2 (477 mg, 0.68 mmol) were added and phenylacetylene (1.86 g, 18.9 mmol) was added dropwise. After stirring at ambient temperature for 16 h, GC/MS showed the reaction was complete. The mixture was filtered through Celite™, the filter pad was washed thoroughly with ethyl acetate, and the combined filtrates were concentrated in vacuo. The residue was dissolved in ethyl acetate (100 mL), washed with water (100 mL), brine (100 mL), dried over Na2SO4, filtered and concentrated in vacuo. The residue was purified by column chromatography eluting with hexane then 95:5 hexane:ethyl acetate to afford 4,5-dimethyl-2-(phenylethynyl)-1,3-thiazole (338 mg 24% yield) as a white solid. M.p. 55–60° C. 1H NMR (CDCl3, 300 MHz) δ 7.56–7.53 (m, 2H), 7.35–7.33 (m, 3H), 2.38 (s, 6H). MS (ESI) 214.0 (M++H).

EXAMPLE 15

5-Methyl-3-[(E)-2-phenylethenyl]-1,2,4-oxadiazole

The title compound was prepared in several steps, with the preparation of key intermediate steps set forth herein as follows:

Preparation of (2E)-N-Hydroxy-3-phenyl-2-propenimidamide: To a solution of hydroxylamine hydrochloride (690 mg, 10 mmol) in ethanol was added NaOH (400 mg, 10 mmol), followed by cinnamonitrile (1.3 g, 10 mmol). This mixture was heated to reflux for 16 h. The ethanol was removed in vacuo, the residue was acidified with 3M HCl (5 mL) and the solution was boiled for 30 minutes. The cooled solution was made basic (pH 8) with NH$_4$OH, and partitioned between water and ethyl acetate. The organics were concentrated to give a sticky white mass which was used without further purification.

Preparation of 5-Methyl-3-[(E)-2-phenylethenyl]-1,2,4-oxadiazole: (2E)-N-Hydroxy-3-phenyl-2-propenimidamide (1.6 g, 10 mmol) was mixed with excess acetyl chloride (30 mL), and heated to reflux. After 1 h the solution was cooled and the excess acetyl chloride was removed in vacuo. The resultant solids were triturated in hot ethyl acetate-hexane-acetone solution, and the supernatant was removed. The remaining solids were dried under high vacuum to afford 5-methyl-3-[(E)-2-phenylethenyl]-1,2,4-oxadiazole (0.50 g, 27% yield from cinnamonitrile) as a pale yellow powder. M.p. 166–168° C. $^1$H NMR (DMSO-d$_6$, 300 MHz) δ 7.59 (m, 3H), 7.42 (m, 3H), 6.58 (d, J=16 Hz, 1H), 2.17 (s, 3H).

EXAMPLE 16

5-[(E)-2-phenylethenyl]-1,2,4-oxadiazole

The title compound was prepared in several steps, with the preparation of key intermediate steps set forth herein as follows:

Preparation of N-[(Dimethylamino)methylene]-cinnamamide: Cinnamamide (4.4 g, 30 mmol) and N,N-dimethylformamide dimethylacetal (9.9 mL, 75 mmol) were heated at reflux for 2 h. Excess formamide and methanol formed in the reaction were removed in vacuo. The solids which formed were collected and washed with hexane, followed by two portions of ethyl acetate, then dried under vacuum at 40° C. to afford N-[(dimethylamino)methylene]-cinnamamide (3.5 g, 58% yield) as a white crystalline solid. M.p. 91–93° C. $^1$H NMR (DMSO-d$_6$, 300 MHz) δ 8.58 (s, 1H), 7.83 (d, J=16 Hz, 1H), 7.57 (m, 2H), 7.36 (m, 3H), 6.74 (d, J=16 Hz, 1H), 3.18 (m, 6H).

Preparation of N-[(Hydroxyamino)methylene]-cinnamamide: N-[(Dimethylamino)methylene]-cinnamamide (1.0 g, 5.0 mmol) was added to a solution of hydroxylamine hydrochloride (415 mg, 6.0 mmol) in acetic acid (5 mL of 70% aqueous) and aqueous NaOH (1.2 mL, 5 M, 6.0 mmol). After stirring for 1.5 h water (5 mL) was added, and the reaction mixture was cooled to 5° C. in an ice bath. The solution was partitioned between ethyl acetate and water, and the organics were dried over Na$_2$SO$_4$, then concentrated in vacuo to afford N-[ (hydroxyamino)methylene]-cinnamamide (850 mg, 90%). This material was carried on to the next step without further purification.

Preparation of 5-[(E)-2-phenylethenyl]-1,2,4-oxadiazole: N-[(Hydroxyamino)methylene]-cinnamamide (850 mg, 4.5 mmol) was dissolved in acetic acid/dioxane (20 mL 1:1 v:v), and heated to reflux for 2 h. The cooled solution was made basic (pH 8) with K$_2$CO$_3$, and partitioned between ethyl acetate and water. The organics were dried over Na$_2$SO$_4$, and concentrated in vacuo. The resultant solids were triturated with hot ethyl acetate, and the soluble portion was purified by flash column chromatography on silica eluting with 2:1 hexane:ethyl acetate to afford 5-[(E)-2-phenylethenyl]-1,2,4-oxadiazole (60 mg, 8% yield) as a white powder. M.p. 53–55° C. 1H NMR (CDCl3, 300 MHz) δ8.43 (s, 1H), 7.85 (d, J=16 Hz, 1H), 7.60 (m, 2H), 7.45 (m, 3H), 7.05 (d, J=16 Hz, 1H). MS (EI ionization) 171 (M$^+$-H).

EXAMPLE 17

Preparation of 1-Methyl-5-[(E)-2-phenylethenyl]-1H-1,2,4-triazole

N-[(Dimethylamino)methylene]-cinnamamide (2.0 g, 10 mmol) was added to a mixture of acetic acid (20 mL) and methylhydrazine (0.6 mL, 11 mmol). The mixture was heated to 90° C. for 2 h. The cooled mixture was concentrated in vacuo, and made basic (pH 9) with solid $K_2CO_3$. The aqueous residue was partitioned between ethyl acetate and water, the organics were dried over $Na_2SO_4$, and concentrated in vacuo. The resultant powder was recrystallized from a minimum of boiling Ethyl acetate. The collected solids were triturated and washed with ethyl acetate to afford 1-methyl-5-[(E)-2-phenylethenyl]-1H-1,2,4-triazole (0.9 g, 49% yield) as a pale yellow powder. M.p. 67–70° C. from Ethyl acetate. $^1$H NMR (CDCl$_3$, 300 MHz) δ 7.88 (s, 1H), 7.73 (d, J=16 Hz, 1H), 7.57 (m, 2H), 7.39 (m, 3H), 6.92 (d, J=16 Hz, 1H), 3.96 (s, 3H).

EXAMPLE 18

3-Methyl-5-[(E)-2-phenylethenyl]-1H-1,2,4-triazole

The title compound was prepared in several steps, with the preparation of key intermediate steps set forth herein as follows:

Preparation of N-[(Dimethylamino)ethylidene]-cinnamamide: Cinnamamide (1.8 g, 12 mmol) and N,N-dimethylacetamide dimethylacetal (2.8 mL, 19 mmol) were heated to 120° C. for 2 h. Excess amide and methanol formed in the reaction were removed in vacuo. The resultant material was purified by flash column chromatography on silica eluting with ethyl acetate to afford N[(dimethylamino)ethylidene]-cinnamamide (2.1 g, 78% yield) as a pale yellow solid containing one equivalent of ethyl acetate. $^1$H NMR (DMSO-d$_6$, 300 MHz) δ 7.61 (d, J=16 Hz, 1H), 7.53 (m, 2H), 7.36 (m, 3H), 6.68 (d, J=16 Hz, 1H), 3.13 (app d, J=15 Hz, 6H), 2.30 (s, 3H).

Preparation of 3-Methyl-5-[(E)-2-phenylethenyl]-1H-1,2,4-triazole: N-[(Dimethylamino)ethylidene]-cinnamamide (2.0 g, 9.0 mmol) was added to a solution of hydrazine hydrate (0.59 mL, 10 mmol) and acetic acid (25 mL). The mixture was heated to 90° C. for 3 h, cooled, and concentrated in vacuo. The resulting material was basified (pH 8) with solid $K_2CO_3$, and partitioned between ethyl acetate and water. The organics were dried over $Na_2SO_4$ and concentrated in vacuo. The resultant material was purified by flash column chromatography on silica eluting with 1:2 hexane-ethyl acetate to afford 3-methyl-5-[(E)-2-phenylethenyl]-1H-1,2,4-triazole (1.6 g, 96% yield) as a white powder. M.p. 131–134° C. $^1$H NMR (CDCl$_3$,300 MHz) δ 7.68 (d, J=16 Hz, 0.3H), 7.59 (d, J=16 Hz, 0.7H), 7.49 (m, 2H), 7.32 (m, 3H), 7.05 (d, J=16 Hz, 1H), 6.49 (d, J=16 Hz, 0.4H), 6.21 (br s, 0.3H), 5.88 (br s, 0.3H), 2.53 (s, 3H). MS (EI ionization) 184 (M$^+$–H).

EXAMPLE 19

Ethyl 3-[(E)-2-phenylethenyl]-1,2,4-thiadiazole-5-carboxylate

The title compound was prepared in several steps, with the preparation of key intermediate steps set forth herein as follows:

Preparation of 5-[(E)-2-Phenylethenyl]-1,3,4-oxathiazol-2-one: Cinnamamide (1.9 g, 13 mmol) was mixed with chlorocarbonylsulphenylchloride (1.0 mL, 13 mmol) in chloroform and heated to reflux for 18 h. The reaction mixture was concentrated in vacuo and the resultant material was taken up in boiling hexane (100 mL). The solvent was decanted from the remaining solid, the volume of this solution was reduced by half, and the solution was allowed to cool. The crystalline solids which formed were collected and washed with hexane to afford 5-[(E)-2-phenylethenyl]-1,3,4-oxathiazol-2-one (1.93 g, 72% yield) as pale yellow needles. M.p. 105–106° C. $^1$H NMR (DMSO-d$_6$, 300 MHz) δ 7.52 (m, 3H), 7.46 (s, 0.5H), 7.41 (m, 2.5H), 6.63 (d, J=16 Hz, 1H).

Preparation of Ethyl 3-[(E)-2-phenylethenyl]-1,2,4-thiadiazole-5-carboxylate: 5-[(E)-2-Phenylethenyl]-1,3,4-oxathiazol-2-one (1.4 g, 7.0 mmol) was mixed with ethyl cyanoformate (2.4 g, 25 mmol) in xylenes, and heated to reflux for 3 h. The reaction mixture was concentrated in vacuo, and the resulting material was recrystallized from ethyl acetate-ethanol (1:1) to give ethyl 3-[(E)-2-phenylethenyl]-1,2,4-thiadiazole-5-carboxylate (1.2 g, 66% yield) as a light yellow solid. M.p. 79–80° C. $^1$H NMR (CDCl$_3$, 300 MHz) δ 7.98 (d, J=16 Hz, 1H), 7.61 (m, 2H), 7.40 (m, 3H), 7.29 (d, J=11 Hz, 1H), 4.56 (q, J=7 Hz, 2H), 1.50 (t, J=7 Hz, 3H). MS (EI ionization) 259 (M$^+$–H).

EXAMPLE 20

{3-[(E)-2-phenylethenyl]-1,2.4-thiadiazol-5-yl}methanol:

Ethyl 3-[(E)-2-phenylethenyl]-1,2,4-thiadiazole-5-carboxylate (1.0 g, 3.8 mmol) was suspended in methanol (50 mL), and NaBH$_4$ (220 mg, 5.8 mmol) was added in portions. The mixture was stirred for 16 h at ambient temperature. The reaction was concentrated in vacuo, acidified with aqueous HCl (4 M) to pH 2, and partitioned between Ethyl acetate and water. The organics were dried over $Na_2SO_4$, concentrated in vacuo, and the resultant material was rerystallized from ethyl acetate to afford {3-[(E)-2-phenylethenyl]-1,2,4-thiadiazol-5-yl}methanol (0.6 g, 71% yield) as a pale yellow solid. M.p. 119–120° C. $^1$H NMR (CDCl$_3$, 300 MHz) δ 7.79 (d, J=16 Hz, 1H), 7.57 (m, 2H), 7.38 (m, 3H), 7.23 (d, J=16 Hz, 1H), 5.14 (d, J=5 Hz, 2H), 3.29 (t, J=5 Hz, 1H). MS (EI ionization) 217 (M$^+$–H).

EXAMPLE 21

2-(1-Cyclohexen-1-ylethynyl)-5-methylthiophene

2-Iodo-5-methylthiophene (1.0 g, 4.5 mmol) was mixed with PdCl$_2$ (44 mg, 0.25 mmol), PPh$_3$ (200 mg, 0.75 mmol), CuI (140 mg, 0.75 mmol) and $K_2CO_3$ (1.66 g, 12 mmol) in a solution of DME and water (1:1). Argon gas was bubbled through the suspension for twenty minutes to deoxygenate the mixture. 1-Ethynyl-1-cyclohexene (1.06 g, 10.0 mmol) was added and the mixture was heated to reflux. After 16 hours the reaction was cooled and filtered through Celite™. The resultant solution was partitioned between water and ethyl acetate. The organic layer was dried over anhydrous $Na_2SO_4$, and concentrated in vacuo. The resulting product was purified by flash column chromatography on silica gel eluting with hexane to afford 2-(1-cyclohexen-1-ylethynyl)-5-methylthiophene (0.96 g, 86% yield) as a light yellow oil. $^1$H NMR (CDCl$_3$, 300 MHz) δ 6.94 (d, J=3.5 Hz, 1H), 6.60 (m, 1H), 6.18 (m, 1H), 2.45 (s, 3H), 2.13 (m, 4H), 1.68–1.57 (m, 4H). MS (EI ionization) 202 (M$^+$).

EXAMPLE 22

Calcium Flux Assay

The activity of compounds was examined against the hmGluR5a receptor stably expressed in mouse fibroblast Ltk cells (the hmGluR5a/L38-20 cell line). See generally Daggett et al., *Neuropharmacology* 34:871–886 (1995). Receptor activity was detected by changes in intracellular calcium ($[Ca^{++}]_i$) measured using the fluorescent calcium-sensitive dye, fura-2. hmGluR5a/L38-20 cells were plated onto 96-well plates, and loaded with 3 µM fura-2 for 1 h. Unincorporated dye was washed from the cells, and the cell plate was transferred to a custom-built 96-channel fluorimeter (SIBIA-SAIC, La Jolla, Calif.) which is integrated into a fully automated plate handling and liquid delivery system. Cells were excited at 350 and 385 nm with a xenon source combined with optical filters. Emitted light was collected from the sample through a dichroic mirror and a 510-nm interference filter and directed into a cooled CCD camera (Princeton Instruments). Image pairs were captured approximately every 1 s, and ratio images were generated after background subtraction. After a basal reading of 20 s, an $EC_{80}$ concentration of glutamate (10 µM) was added to the well, and the response evaluated for another 60 s. The glutamate-evoked increase in $[Ca^{++}]_i$ in the presence of the screening compound was compared to the response of glutamate alone (the positive control). Results from this assay are presented in Table 1.

EXAMPLE 23

Phosphatidylinositol Hydrolysis ($IP_1$)Assays

Inositol phophate assays were performed as described by Berridge et al. (1982) (Berridge et al, (1982) *Biochem. J.* 206:587–5950; and Nakajima et al., *J. Biol. Chem.* 267: 2437–2442 (1992)) with slight modifications. Mouse fibroblast Ltk cells expressing hmGluR5 (hmGluR5/L38-20 cells) were seeded in 24-well plates at a density of $8 \times 10^5$ cells/well. One µCi of [$^3$H]-inositol (Amersham PT6-271; Arlington Heights, Ill.; specific activity=17.7 Ci/mmol) was added to each well and incubated for 16 h at 37° C. Cells were washed twice and incubated for 45 min in 0.5 ml of standard Hepes buffered saline buffer (HBS; 125 mM NaCl, 5 mM KCl, 0.62 mM $MgSO_4$, 1.8 mM $CaCl_2$, 20 mM HEPES, 6 mM Glucose, pH to 7.4). The cells were washed with HBS containing 10 mM LiCl, and 400 µl buffer added to each well. Cells were incubated at 37° C. for 20 min. For testing, 50 µl of 10X compounds used in the practice of the invention (made in HBS/LiCl (100 mM)) was added and incubated for 10 minutes. Cells were activated by the addition of 10 µM glutamate, and the plates left for 1 hour at 37° C.

The incubations were terminated by the addition of 1 ml ice-cold methanol to each well. In order to isolate inositol phosphates (IPs), the cells were scraped from wells, and placed in numbered glass test tubes. One ml of chloroform was added to each tube, the tubes were mixed, and the phases separated by centrifugation. IPs were separated on Dowex anion exchange columns (AG 1-X8 100–200 mesh formate form). The upper aqueous layer (750 ul) was added to the Dowex columns, and the columns eluted with 3 ml of distilled water. The eluents were discarded, and the columns were washed with 10 mls of 60 mM ammonium formate/5 mM Borax, which was also discarded as waste. Finally the columns were eluted with 4 ml of 800 mM ammonium formate/0.1 M formic acid, and the samples collected in scintillation vials. Scintillant was added to each vial, and the vials shaken, and counted in a scintillation counter after 2 hours. Phosphatidylinositol hydrolysis in cells treated with test compounds was compared to phosphatidylinositol hydrolysis in cells treated with control and the results are shown in Table 1.

EXAMPLE 24

Analgesic Animal Model (CFA Model)

Compounds that modulate receptor-mediated analgesic responses wer tested in an animal model. Robust inflammation was induced by the injection of complete Freund's adjuvant (CFA, 10 mg/ml) subcutaneously into the hind paw of male Sprague-Dawley rats (150–175 g). The inflammatory response to CFA began approximately 12-hrs post-CFA injection and persisted for several days following inoculation. The inflamed hind paw became sensitive to noxious (paw pinch, plantar test) or innocuous (cold plate, Von Frey filaments) stimuli compared to the contralateral hind paw. Test compounds (240 µmol/kg) were administered via intraperitoneal injection. The analgesic activity of compounds was evaluated one to 24-hours post administration by assessing (1) the duration of analgesic effect; (2) threshold to elicit response; and (3) time from painful stimulus to response. A general increase in duration of analgesic effect, threshold to painful stimuli or time to respond following drug administration suggested analgesic efficacy. For each group of animals, responses following drug administration were compared to responses prior to drug administration. Results are presented in Table 1.

TABLE 1

| Example (Compound) | $Ca^{2+}$ Flux | PI Hydrolysis | CFA Model |
|---|---|---|---|
| 1 | +/− | +/− | NT |
| 2 | ++ | +/− | NT |
| 3 | + | + | + |
| 4 | +++ | +++ | ++ |
| 5 | ++ | ++ | NT |
| 6 | ++ | +/− | +/− |
| 7 | + | − | NT |
| 8 | +++ | ++ | +++ |
| 9 | ++ | + | NT |
| 10 | − | − | NT |
| 11 | ++ | ++ | ++ |
| 12 | + | + | NT |
| 13 | ++ | ++ | NT |
| 14 | +++ | + | NT |
| 15 | − | − | NT |
| 16 | − | − | NT |
| 17 | − | − | NT |
| 18 | − | − | NT |
| 19 | + | +/− | NT |
| 20 | +/− | − | NT |
| 21 | − | − | NT |

$Ca^{2+}$ Flux: +++: $IC_{50} \leq 10$ nmol; ++: 10 nmol $\leq IC_{50} \leq 100$ nmol; +: 100 nmol $\leq IC_{50} \leq 1$ µmol; +/−: 1 µmol $\leq IC_{50} \leq 10$ µmol; −: $IC_{50} > 10$ µmol.
PI Hydrolysis: +++: $IC_{50} \leq 100$ nmol; ++: 100 nmol $\leq IC_{50} \leq 1$ µmol; +: 1 µmol $\leq IC_{50} \leq 10$ µmol; +/−: 10 µmol $\leq IC_{50} \leq 100$ µmol; −: $IC_{50} > 100$ µmol.
CFA Model: +++ = high analgesic efficacy; NT = not tested.

Data presented in Table 1 demonstrate that the activity of metabotropic glutamate receptor 5 (mGluR5), assessed by measuring receptor-activated changes in calcium flux may be modulated by compounds contemplated in the practice of the invention. In assays using cells transfected with mGluR5a, a majority of compounds were effective at decreasing intracellular calcium flux, and decreasing phosphoinositol hydrolysis.

EXAMPLE 25

Salt forms of 2-(Phenylethynyl)-1,3-thiazole

Various salt forms of 2-(phenylethynyl)-1,3-thiazole were prepared, and their solubility, hygroscopicity, and physical state were assessed. The compound 2-phenylethynl-1,3-thiazole was prepared (see Example 8) as well as hydrochloric acid, fumaric acid, methylsulfonic acid and toluene sulfonic acid salt forms of the compound. The hydrochloric acid salt form of 2-(phenylethynyl)-1,3-thiazole is an oil. A fumaric acid salt form was not obtained by preparative steps including trituration with diethylether. Preparation of the methylsulfonate form results in a semi solid, hygroscopic material. These salt forms are typically unsuitable for certain pharmaceutical formulations, such as for tablets, capsules, and the like. In contrast to the salt forms of 2-(phenylethynyl)-1,3-thiazole, described previously, the tosylate salt form (i.e., the toluene sulfonic acid salt) is a solid having a melting point of about 129 up to 131° C. and is non-hygroscopic. Therefore, this form is presently preferred for pharmaceutical formulations of tablets, capsules, and the like.

While the invention has been described in detail with reference to certain preferred embodiments thereof, it will be understood that modifications and variations are within the spirit and scope of that which is described and claimed.

What is claimed is:

1. A method of modulating the activity of metabotropic glutamate receptors, said method comprising:
   contacting said receptors with at least one compound having the structure A-L-B or enantiomers, diastereomeric isomers or mixtures of any two or more thereof, or pharmaceutically acceptable salts thereof, in an amount sufficient to modulate the activity of metabotropic glutamate receptors wherein:
   A is thiazolyl optionally substituted with 1 or 2 independent halogen, substituted or unsubstituted hydrocarbyl, substituted or unsubstituted aryl, heterocycle, mercapto, nitro, carboxyl, carbamate, carboxamide, hydroxy, ester, cyano, amine, amide, amidine, amido, sulfonyl or sulfonamide;
   L is alkynylene; and
   B is substituted or unsubstituted aryl,
   wherein said aryl substituents are selected from lower alkyl, lower ankenyl, lower alkynyl, hydroxy, hydroxy-lower alkynyl, lower alkoxy, lower alkenyloxy, lower akenylenedioxy, lower alkanoyloxy, phenoxy, phenyl-lower alkoxy, acyl, carboxy, esterified carboxy, amidated carboxy, cyano, nitro, amino, acylamino, N-acyl-N-lower alkylamino, halo, halo-lower alkyl, and wherein phenyl, phenyl lower alkynyl, phenoxy, and phenyl lower-alkoxy are optionally substituted.

2. A method for treating a disease condition which is treatable by modulation of the activity of metabotropic glutamate receptors, said method comprising: administering to a patent having said disease condition, a therapeutically effective amount which is sufficient to modulate the activity of metabotropic glutamate receptors, of at least one compound having the structure A-L-B or enantiomers, diastereomeric isomers or mixtures of any two or more thereof, or pharmaceutically acceptable salts thereof, wherein:
   A is thiazolyl optionally substituted with 1 or 2 independent halogen, substituted or unsubstituted hydrocarbyl, substituted or unsubstituted aryl, heterocycle, mercapto, nitro, carboxyl, carbamate, carboxamide, hydroxy, ester, cyano, amine, amide, amidine, amido, sulfonyl or sulfonamide;
   L is alkynylene; and
   B is substituted or unsubstituted aryl,
   wherein said aryl substituents are selected from lower alkyl, lower ankenyl, lower alkynyl, hydroxy, hydroxy-lower alkynyl, lower alkoxy, lower alkenyloxy, lower akenylenedioxy, lower alkanoyloxy, phenoxy, phenyl-lower alkoxy, acyl, carboxy, esterified carboxy, amidated carboxy, cyano, nitro, amino, acylamino, N-acyl-N-lower alkylamino, halo, halo-lower alkyl, and wherein phenyl, phenyl lower alkynyl, phenoxy, and phenyl lower-alkoxy are optionally substituted.

3. The method according to claim 2, wherein said disease condition is neuropathic pain, chronic pain, acute pain, painful diabetic neuropathy, post-herpetic neuralgia, cancer-associated pain, pain associated with chemotherapy, pain associated with spinal cord injury, pain associated with multiple sclerosis, causalgia and reflex sympathetic dystrophy, phantom pain, post-stroke (central) pain, pain associated with HIV or AIDS, trigeminal neuralgia, lower back pain, myofacial disorders, migraine, osteoarthritic pain, postoperative pain, dental pain, post-burn pain, pain associated with systemic lupus, entrapment neuropathies, painful polyneuropathies, ocular pain, pain associated with inflammation or pain due to tissue injury.

4. A method for preventing pain in a subject at risk thereof, said method comprising: administering to a patent having said disease condition, a therapeutically effective amount which is sufficient to modulate the activity of metabotropic glutamate receptors, of at least one compound having the structure A-L-B or enantiomers, diastereomeric isomers or mixtures of any two or more thereof, or pharmaceutically acceptable salts thereof, wherein:
   A is thiazolyl optionally substituted with 1 or 2 independent halogen, substituted or unsubstituted hydrocarbyl, substituted or unsubstituted aryl, heterocycle, mercapto, nitro, carboxyl, carbamate, carboxamide, hydroxy, ester, cyano, amine, amide, amidine, amido, sulfonyl or sulfonamide;
   L is alkynylene; and
   B is substituted or unsubstituted aryl,
   wherein said aryl substituents are selected from lower alkyl, lower ankenyl, lower alkynyl, hydroxy, hydroxy-lower alkyny, lower alkoxy, lower alkenyloxy, lower akenylenedioxy, lower alkanoyloxy, phenoxy, phenyl-lower alkoxy, acyl, carboxy, esterified carboxy, amidated carboxy, cyano, nitro, amino, acylamino, N-acyl-N-lower alkylamino, halo, halo-lower alkyl,
   and wherein phenyl, phenyl lower alkynyl, phenoxy, and phenyl lower-alkoxy are optionally substituted.

5. A pharmaceutically acceptable salt form of the compound [according to claim 1, wherein] A-L-B, wherein:
   A is thiazolyl optionally substituted with 1 or 2 independent halogen, substituted or unsubstituted hydrocarbyl, substituted or unsubstituted aryl, heterocycle, mercapto, nitro, carboxyl, carbamate, carboxamide, hydroxy, ester, cyano, amine, amide, amidine, amido, sulfonyl or sulfonamide;
   L is alkynylene; and
   B is substituted or unsubstituted aryl,
   wherein said aryl substituents are selected from lower alkyl, lower ankenyl, lower alkynyl, hydroxy, hydroxy-lower alkynyl, lower alkoxy, lower alkenyloxy, lower akenylenedioxy, lower alkanoyloxy, phenoxy, phenyl-lower alkoxy, acyl, carboxy, esterified carboxy, amidated carboxy, cyano, nitro, amino, acylamino, N-acyl-N-lower alkylamino, halo, halo-lower alkyl, and wherein phenyl, phenyl lower alkynyl, phenoxy, and phenyl lower-alkoxy are optionally substituted,
wherein the salt is a toluene sulfonic acid salt.

6. The compound which is 2-methyl-4(phenyl ethynyl)-1,3-thiazole, and pharmaceutically acceptable salts thereof.

7. The compound of claim 6 which is 2-methyl-4(phenyl ethynyl)-1,3-thiazole p-toluene sulfonic acid salt.

* * * * *